United States Patent [19]

Lehrer et al.

[11] Patent Number: 5,693,486
[45] Date of Patent: Dec. 2, 1997

[54] DNA SEQUENCES ENCODING PROTEGRINS AND PROTEGRIN ANALOGS AND THEIR USE IN RECOMBINANT METHODS OF PRODUCING PROTEGRINS

[75] Inventors: Robert L. Lehrer, Santa Monica; Vladimir N. Kokryakov, Los Angeles; Sylvia S. L. Harwig, Woodland Hills, all of Calif.

[73] Assignee: IntraBiotics, Sunnyvale, Calif.

[21] Appl. No.: 182,483

[22] Filed: Jan. 13, 1994

Related U.S. Application Data

[63] Continuation-in-part of Ser. No. 95,769, Jul. 26, 1993, Pat. No. 5,464,823, which is a continuation-in-part of Ser. No. 93,926, Jul. 20, 1993, abandoned.

[51] Int. Cl.[6] .......................... C12N 15/12; C12N 15/70; C07K 7/00; C07K 7/08
[52] U.S. Cl. .................. 435/69.1; 435/252.3; 435/320.1; 530/321; 530/323; 530/326; 536/23.5; 935/11; 935/29; 935/60; 935/73
[58] Field of Search ....................... 530/321, 323, 530/326; 536/23.5; 435/69.1, 252.3, 320.1

[56] References Cited

U.S. PATENT DOCUMENTS

| | | | |
|---|---|---|---|
| 4,652,639 | 3/1987 | Stabinsky | 435/69.1 |
| 5,432,270 | 7/1995 | Zasloff et al. | 536/23.5 |
| 5,459,235 | 10/1995 | Selsted et al. | 530/300 |
| 5,464,823 | 11/1995 | Lehrer et al. | 514/13 |

FOREIGN PATENT DOCUMENTS

| | | |
|---|---|---|
| 0 545 730 A1 | 6/1993 | European Pat. Off. . |
| WO 89/11291 | 11/1989 | WIPO . |
| WO 93/24139 | 12/1993 | WIPO . |
| WO 94/21672 | 9/1994 | WIPO . |
| WO 95/03325 | 2/1995 | WIPO . |
| WO 95/10534 | 4/1995 | WIPO . |

OTHER PUBLICATIONS

Matsumoto, S., et al., Chemical and Pharmaceutical Bulletin, vol. 40, No. 10, pp. 2701–2706, 1992.

Tamamura, H. et al., "A comparative study of the solution structures of tachyplesin I and a novel anti–HIV synthetic peptide, T22 ([Tyr$^{5,12}$, Lys$^{7}$]-polyphemusin II), determined by nuclear magnetic resonance," *Biochimica et Biophysica Acta* (1993) 1163:209–216.

Tamamura, H. et al. "Antimicrobial Activity and Conformation of Tachyplesin I and Its Analogs," *Chem Pharm Bull* (1993) 41(5):978–980.

Zhao, C. et al., "Identification of a new member of the protegrin family by cDNA cloning," *FEBS Letters* (1994) 346:285–288.

Lehrer et al., Direct Inactivation of Viruses by MCP–1 an MCP–2 Natural Peptide Antibiotics from Rabbit Leukocytes; J. Virol. (1985) 54:467–472.

Mirgorodskaya, et al., Primary structure of three cationic peptides from porcine neutrophils; FEBS (1993) 330:339–342.

Storici, et al., A Novel cDNA Sequence Encoding a Pig Leukocyte Antimicrobial Peptide with a Cathelin–like Pro-sequence; Biochem. Biophys. Res. Comm. (1993) 196:1363–1367.

Rustici et al., Molecular Mapping and Detoxification of the Lipid A Binding Site by Synthetic Peptides; Science (1993) 259:361–364.

Matsuzaki et al., Role of Disulfide Linkages in Tachytoplesin—Lipid Interactions; Biochemistry (1993) 32:11704–11710.

Hoess et al., EMBO J. (1993) 12:3351–3356.

Elsbach et al., Current Opinion in Immunology (1993) 5:103–107.

Kokryakov et al.; Protegrins: leukocyte antimicrobial peptides that combine features of corticostatic defensins and tachyplesins; FEBS 327(2):231–236 (1993).

Selsted et al.; Primary structures of six antimicrobial peptides of rabbit peritoneal neutrophils; J. Biol. Chem. 260(8):4579–4584 (1985).

*Primary Examiner*—Robert A. Wax
*Assistant Examiner*—William W. Moore
*Attorney, Agent, or Firm*—Morrison & Foerster LLP

[57] ABSTRACT

Peptide-based compounds containing four invariant cysteine residues which have been optionally oxidized to contain two intramolecular disulfide bonds, or modified forms where the cysteines are replaced, are useful as preservatives and in preventing, treating, or ameliorating viral or microbial infection in animals and plants, and in inactivating endotoxin. These compounds, in one embodiment, are of the formula:

$$A_1-A_2-A_3-A_4-A_5-C-A_7-C-A_9-A_{10}-A_{11}-A_{12}-C-A_{14}-C-A_{16}-(A_{17}-A_{18}) \quad \text{(1)(SEQ ID NO:1)}$$

and the N-terminal acylated and/or C-terminal amidated or esterified forms thereof, either in optionally —SH stabilized linear or in cystine-bridged form wherein $A_1$, $A_9$, $A_{10}$, and $A_{11}$ are basic amino acids;

$A_2$ and $A_3$ are small amino acids;

$A_5$, $A_7$, $A_{12}$, $A_{14}$ and $A_{16}$ are hydrophobic amino acids; and $A_4$ is a basic or a small amino acid;

$A_{17}$ is not present or, if present, is a small amino acid;

$A_{18}$ is not present or, if present, is a basic amino acid, and modified form of formula (1) SEQ ID NO:1) wherein each of 1–4 cysteines is independently replaced by a hydrophobic amino acid or a small amino acid.

17 Claims, 11 Drawing Sheets

SEQUENCE LISTING ( 1 ) GENERAL INFORMATION:

( i i i ) NUMBER OF SEQUENCES: 31

( 2 ) INFORMATION FOR SEQ ID NO:1:

( i ) SEQUENCE CHARACTERISTICS:
        ( A ) LENGTH: 18 amino acids
        ( B ) TYPE: amino acid
        ( C ) STRANDEDNESS: single
        ( D ) TOPOLOGY: linear ( i x ) FEATURE:
        ( A ) NAME/KEY: Modified-site
        ( B ) LOCATION: group(1, 9, 10, 11)
        ( D ) OTHER INFORMATION: /label= A1- A9-A10-A11
            / note= "A1, A9, A10 and A11 are any basic amino acids"

( i x ) FEATURE:
        ( A ) NAME/KEY: Modified-site
        ( B ) LOCATION: group(2, 3)
        ( D ) OTHER INFORMATION: /label= A2- A3
            / note= "A2 and A3 are any small amino acids"

( i x ) FEATURE:
        ( A ) NAME/KEY: Modified-site
        ( B ) LOCATION: 4

( D ) OTHER INFORMATION: /label=A4
                    / note= "X is any basic or small amino acid"

( i x ) FEATURE:
             ( A ) NAME/KEY: Modified-site
             ( B ) LOCATION: group(5, 7, 12, 14, 16)
             ( D ) OTHER INFORMATION: /label= A5- 7-12-14-A16
                    / note= "A5, A7, A12, A14 and A16 are any hydrophobic
                      amino acids"

( i x ) FEATURE:
             ( A ) NAME/KEY: Modified-site
             ( B ) LOCATION: 17
             ( D ) OTHER INFORMATION: /label=A17
                    / note= "A17 is either a small amino acid or not present"

( i x ) FEATURE:
             ( A ) NAME/KEY: Modified-site
             ( B ) LOCATION: 18
             ( D ) OTHER INFORMATION: /label=A18
                    / note= "A18 is not present if A17 is not present; If A17
                      is present, A18 may be not present or a basic amino
                      acid."

( x i ) SEQUENCE DESCRIPTION: SEQ ID NO:1:

Xaa  Xaa  Xaa  Xaa  Xaa  Cys  Xaa  Cys  Xaa  Xaa  Xaa  Xaa  Cys  Xaa  Cys  Xaa
     1                  5                             10                          15

Xaa  Xaa ( 2 ) INFORMATION FOR SEQ ID NO:2:

( i ) SEQUENCE CHARACTERISTICS:
             ( A ) LENGTH: 18 amino acids
             ( B ) TYPE: amino acid
             ( C ) STRANDEDNESS: single
             ( D ) TOPOLOGY: linear ( x i ) SEQUENCE DESCRIPTION: SEQ ID NO:2:

Arg  Gly  Gly  Arg  Leu  Cys  Tyr  Cys  Arg  Arg  Arg  Phe  Cys  Val  Cys  Val
     1                  5                             10                          15

Gly  Arg ( 2 ) INFORMATION FOR SEQ ID NO:3:

( i ) SEQUENCE CHARACTERISTICS:
             ( A ) LENGTH: 16 amino acids
             ( B ) TYPE: amino acid
             ( C ) STRANDEDNESS: single
             ( D ) TOPOLOGY: linear ( x i ) SEQUENCE DESCRIPTION: SEQ ID NO:3:

Arg  Gly  Gly  Arg  Leu  Cys  Tyr  Cys  Arg  Arg  Arg  Phe  Cys  Ile  Cys  Val
     1                  5                             10                          15

( 2 ) INFORMATION FOR SEQ ID NO:4:

( i ) SEQUENCE CHARACTERISTICS:
             ( A ) LENGTH: 18 amino acids
             ( B ) TYPE: amino acid
             ( C ) STRANDEDNESS: single
             ( D ) TOPOLOGY: linear ( x i ) SEQUENCE DESCRIPTION: SEQ ID NO:4:

Arg  Gly  Gly  Gly  Leu  Cys  Tyr  Cys  Arg  Arg  Arg  Phe  Cys  Val  Cys  Val
     1                  5                             10                          15

Gly  Arg ( 2 ) INFORMATION FOR SEQ ID NO:5:

( i ) SEQUENCE CHARACTERISTICS:
   ( A ) LENGTH: 16 amino acids
   ( B ) TYPE: amino acid
   ( C ) STRANDEDNESS: single
   ( D ) TOPOLOGY: linear ( x i ) SEQUENCE DESCRIPTION: SEQ ID NO:5:

Arg Gly Gly Arg Leu Cys Tyr Cys Arg Arg Arg Phe Cys Val Cys Val
1               5                   10                  15

( 2 ) INFORMATION FOR SEQ ID NO:6:

( i ) SEQUENCE CHARACTERISTICS:
      ( A ) LENGTH: 16 amino acids
      ( B ) TYPE: amino acid
      ( C ) STRANDEDNESS: single
      ( D ) TOPOLOGY: linear ( x i ) SEQUENCE DESCRIPTION: SEQ ID NO:6:

Lys Gly Gly Arg Leu Cys Tyr Cys Arg Arg Arg Phe Cys Val Cys Val
1               5                   10                  15

( 2 ) INFORMATION FOR SEQ ID NO:7:

( i ) SEQUENCE CHARACTERISTICS:
      ( A ) LENGTH: 16 amino acids
      ( B ) TYPE: amino acid
      ( C ) STRANDEDNESS: single
      ( D ) TOPOLOGY: linear ( i x ) FEATURE:
      ( A ) NAME/KEY: Modified-site
      ( B ) LOCATION: 4
      ( D ) OTHER INFORMATION: /product="homoarginine(Har)"

( x i ) SEQUENCE DESCRIPTION: SEQ ID NO:7:

Arg Gly Gly Xaa Leu Cys Tyr Cys Arg Arg Arg Phe Cys Val Cys Val
1               5                   10                  15

( 2 ) INFORMATION FOR SEQ ID NO:8:

( i ) SEQUENCE CHARACTERISTICS:
      ( A ) LENGTH: 18 amino acids
      ( B ) TYPE: amino acid
      ( C ) STRANDEDNESS: single
      ( D ) TOPOLOGY: linear ( i x ) FEATURE:
      ( A ) NAME/KEY: Modified-site
      ( B ) LOCATION: group(4, 9)
      ( D ) OTHER INFORMATION: /product="homoarginine(Har)"

( x i ) SEQUENCE DESCRIPTION: SEQ ID NO:8:

Arg Gly Gly Xaa Leu Cys Tyr Cys Xaa Arg Arg Phe Cys Val Cys Val
1               5                   10                  15

Gly Arg ( 2 ) INFORMATION FOR SEQ ID NO:9:

( i ) SEQUENCE CHARACTERISTICS:
      ( A ) LENGTH: 18 amino acids
      ( B ) TYPE: amino acid
      ( C ) STRANDEDNESS: single
      ( D ) TOPOLOGY: linear ( i x ) FEATURE:
      ( A ) NAME/KEY: Modified-site
      ( B ) LOCATION: 10
      ( D ) OTHER INFORMATION: /product="homoarginine(Har)"

( x i ) SEQUENCE DESCRIPTION: SEQ ID NO:9:

```
Arg Gly Gly Arg Val Cys Tyr Cys Arg Xaa Arg Phe Cys Val Cys Val
1               5                   10                  15
Gly Arg
```

(2) INFORMATION FOR SEQ ID NO:10:

(i) SEQUENCE CHARACTERISTICS:
        (A) LENGTH: 18 amino acids
        (B) TYPE: amino acid
        (C) STRANDEDNESS: single
        (D) TOPOLOGY: linear (xi) SEQUENCE DESCRIPTION: SEQ ID NO:10:

```
Arg Gly Gly Arg Leu Cys Tyr Cys Arg Lys Lys Trp Cys Val Cys Val
1               5                   10                  15
Gly Arg
```

(2) INFORMATION FOR SEQ ID NO:11:

(i) SEQUENCE CHARACTERISTICS:
        (A) LENGTH: 18 amino acids
        (B) TYPE: amino acid
        (C) STRANDEDNESS: single
        (D) TOPOLOGY: linear (ix) FEATURE:
        (A) NAME/KEY: Modified-site
        (B) LOCATION: 10
        (D) OTHER INFORMATION: /product="homoarginine(Har)"

(xi) SEQUENCE DESCRIPTION: SEQ ID NO:11:

```
Arg Gly Gly Arg Leu Cys Tyr Cys Arg Xaa Arg Tyr Cys Val Cys Val
1               5                   10                  15
Gly Arg
```

(2) INFORMATION FOR SEQ ID NO:12:

(i) SEQUENCE CHARACTERISTICS:
        (A) LENGTH: 18 amino acids
        (B) TYPE: amino acid
        (C) STRANDEDNESS: single
        (D) TOPOLOGY: linear (xi) SEQUENCE DESCRIPTION: SEQ ID NO:12:

```
Arg Gly Ser Gly Leu Cys Tyr Cys Arg Arg Lys Trp Cys Val Cys Val
1               5                   10                  15
Gly Arg
```

(2) INFORMATION FOR SEQ ID NO:13:

(i) SEQUENCE CHARACTERISTICS:
        (A) LENGTH: 18 amino acids
        (B) TYPE: amino acid
        (C) STRANDEDNESS: single
        (D) TOPOLOGY: linear (xi) SEQUENCE DESCRIPTION: SEQ ID NO:13:

```
Arg Ala Thr Arg Ile Cys Phe Cys Arg Arg Arg Phe Cys Val Cys Val
1               5                   10                  15
Gly Arg
```

(2) INFORMATION FOR SEQ ID NO:14:

(i) SEQUENCE CHARACTERISTICS:
        (A) LENGTH: 18 amino acids (B) TYPE: amino acid
(C) STRANDEDNESS: single
(D) TOPOLOGY: linear (ix) FEATURE:
(A) NAME/KEY: Modified-site
(B) LOCATION: 10
(D) OTHER INFORMATION: /product="homoarginine(Har)"

(xi) SEQUENCE DESCRIPTION: SEQ ID NO:14:

Arg Gly Gly Lys Val Cys Tyr Cys Arg Xaa Arg Phe Cys Val Cys Val
1               5                   10                  15

Gly Arg (2) INFORMATION FOR SEQ ID NO:15:

(i) SEQUENCE CHARACTERISTICS:
(A) LENGTH: 18 amino acids
(B) TYPE: amino acid
(C) STRANDEDNESS: single
(D) TOPOLOGY: linear (ix) FEATURE:
(A) NAME/KEY: Modified-site
(B) LOCATION: 9
(D) OTHER INFORMATION: /note="D-form of amino acid"

(ix) FEATURE:
(A) NAME/KEY: Modified-site
(B) LOCATION: 18
(D) OTHER INFORMATION: /note="D form of amino acid"

(xi) SEQUENCE DESCRIPTION: SEQ ID NO:15:

Arg Ala Thr Arg Ile Cys Phe Cys Arg Arg Arg Phe Cys Val Cys Val
1               5                   10                  15

Gly Arg (2) INFORMATION FOR SEQ ID NO:16:

(i) SEQUENCE CHARACTERISTICS:
(A) LENGTH: 18 amino acids
(B) TYPE: amino acid
(C) STRANDEDNESS: single
(D) TOPOLOGY: linear (ix) FEATURE:
(A) NAME/KEY: Modified-site
(B) LOCATION: 10
(D) OTHER INFORMATION: /product="homoarginine(Har)"
/ note="D form of amino acid"

(xi) SEQUENCE DESCRIPTION: SEQ ID NO:16:

Arg Gly Gly Lys Val Cys Tyr Cys Arg Xaa Arg Phe Cys Val Cys Val
1               5                   10                  15

Gly Arg (2) INFORMATION FOR SEQ ID NO:17:

(i) SEQUENCE CHARACTERISTICS:
(A) LENGTH: 18 amino acids
(B) TYPE: amino acid
(C) STRANDEDNESS: single
(D) TOPOLOGY: linear (xi) SEQUENCE DESCRIPTION: SEQ ID NO:17:

Arg Gly Gly Arg Leu Val Tyr Cys Arg Arg Arg Phe Cys Val Cys Val
1               5                   10                  15

Gly Arg ( 2 ) INFORMATION FOR SEQ ID NO:18:

( i ) SEQUENCE CHARACTERISTICS:
        ( A ) LENGTH: 16 amino acids
        ( B ) TYPE: amino acid
        ( C ) STRANDEDNESS: single
        ( D ) TOPOLOGY: linear ( x i ) SEQUENCE DESCRIPTION: SEQ ID NO:18:

```
Arg Gly Gly Arg Leu Gly Tyr Cys Arg Arg Arg Phe Cys Ile Cys Val
 1               5                  10                  15
```

( 2 ) INFORMATION FOR SEQ ID NO:19:

( i ) SEQUENCE CHARACTERISTICS:
        ( A ) LENGTH: 18 amino acids
        ( B ) TYPE: amino acid
        ( C ) STRANDEDNESS: single
        ( D ) TOPOLOGY: linear ( x i ) SEQUENCE DESCRIPTION: SEQ ID NO:19:

```
Arg Gly Gly Gly Leu Cys Tyr Gly Arg Arg Arg Phe Cys Val Cys Val
 1               5                  10                  15
Gly Arg
```

( 2 ) INFORMATION FOR SEQ ID NO:20:

( i ) SEQUENCE CHARACTERISTICS:
        ( A ) LENGTH: 16 amino acids
        ( B ) TYPE: amino acid
        ( C ) STRANDEDNESS: single
        ( D ) TOPOLOGY: linear ( x i ) SEQUENCE DESCRIPTION: SEQ ID NO:20:

```
Arg Gly Gly Arg Leu Gly Tyr Gly Arg Arg Arg Phe Gly Val Cys Val
 1               5                  10                  15
```

( 2 ) INFORMATION FOR SEQ ID NO:21:

( i ) SEQUENCE CHARACTERISTICS:
        ( A ) LENGTH: 16 amino acids
        ( B ) TYPE: amino acid
        ( C ) STRANDEDNESS: single
        ( D ) TOPOLOGY: linear ( x i ) SEQUENCE DESCRIPTION: SEQ ID NO:21:

```
Lys Gly Gly Arg Leu Val Tyr Val Arg Arg Arg Phe Ile Val Cys Val
 1               5                  10                  15
```

( 2 ) INFORMATION FOR SEQ ID NO:22:

( i ) SEQUENCE CHARACTERISTICS:
        ( A ) LENGTH: 16 amino acids
        ( B ) TYPE: amino acid
        ( C ) STRANDEDNESS: single
        ( D ) TOPOLOGY: linear ( i x ) FEATURE:
        ( A ) NAME/KEY: Modified-site
        ( B ) LOCATION: 4
        ( D ) OTHER INFORMATION: /product="homoarginine(Har)"

( x i ) SEQUENCE DESCRIPTION: SEQ ID NO:22:

```
Arg Gly Gly Xaa Leu Cys Tyr Cys Arg Arg Arg Phe Cys Val Gly Val
 1               5                  10                  15
```

( 2 ) INFORMATION FOR SEQ ID NO:23:

( i ) SEQUENCE CHARACTERISTICS:
  ( A ) LENGTH: 18 amino acids
  ( B ) TYPE: amino acid
  ( C ) STRANDEDNESS: single
  ( D ) TOPOLOGY: linear ( i x ) FEATURE:
  ( A ) NAME/KEY: Modified-site
  ( B ) LOCATION: group(4, 9)
  ( D ) OTHER INFORMATION: /product="homoarginine(Har)"

( x i ) SEQUENCE DESCRIPTION: SEQ ID NO:23:

Arg Gly Gly Xaa Leu Cys Tyr Cys Xaa Arg Arg Phe Cys Val Leu Val
1               5                   10                  15
Gly Arg ( 2 ) INFORMATION FOR SEQ ID NO:24:

( i ) SEQUENCE CHARACTERISTICS:
  ( A ) LENGTH: 18 amino acids
  ( B ) TYPE: amino acid
  ( C ) STRANDEDNESS: single
  ( D ) TOPOLOGY: linear ( i x ) FEATURE:
  ( A ) NAME/KEY: Modified-site
  ( B ) LOCATION: 10
  ( D ) OTHER INFORMATION: /product="homoarginine(Har)"

( x i ) SEQUENCE DESCRIPTION: SEQ ID NO:24:

Arg Gly Gly Arg Val Cys Tyr Val Arg Xaa Arg Phe Leu Val Gly Val
1               5                   10                  15
Gly Arg ( 2 ) INFORMATION FOR SEQ ID NO:25:

( i ) SEQUENCE CHARACTERISTICS:
  ( A ) LENGTH: 18 amino acids
  ( B ) TYPE: amino acid
  ( C ) STRANDEDNESS: single
  ( D ) TOPOLOGY: linear ( x i ) SEQUENCE DESCRIPTION: SEQ ID NO:25:

Arg Gly Gly Arg Leu Cys Tyr Ser Arg Lys Lys Trp Cys Val Ser Val
1               5                   10                  15
Gly Arg ( 2 ) INFORMATION FOR SEQ ID NO:26:

( i ) SEQUENCE CHARACTERISTICS:
  ( A ) LENGTH: 18 amino acids
  ( B ) TYPE: amino acid
  ( C ) STRANDEDNESS: single
  ( D ) TOPOLOGY: linear ( i x ) FEATURE:
  ( A ) NAME/KEY: Modified-site
  ( B ) LOCATION: 10
  ( D ) OTHER INFORMATION: /product="homoarginine(Har)"

( x i ) SEQUENCE DESCRIPTION: SEQ ID NO:26:

Arg Gly Gly Arg Leu Cys Tyr Cys Arg Xaa Arg Tyr Ser Val Val Val
1               5                   10                  15
Gly Arg ( 2 ) INFORMATION FOR SEQ ID NO:27:

( i ) SEQUENCE CHARACTERISTICS:

(A) LENGTH: 18 amino acids
(B) TYPE: amino acid
(C) STRANDEDNESS: single
(D) TOPOLOGY: linear (xi) SEQUENCE DESCRIPTION: SEQ ID NO:27:

Arg Gly Ser Gly Leu Ser Tyr Cys Arg Arg Lys Trp Gly Val Cys Val
1               5                   10                  15
Gly Arg (2) INFORMATION FOR SEQ ID NO:28:

(i) SEQUENCE CHARACTERISTICS:
(A) LENGTH: 18 amino acids
(B) TYPE: amino acid
(C) STRANDEDNESS: single
(D) TOPOLOGY: linear (xi) SEQUENCE DESCRIPTION: SEQ ID NO:28:

Arg Ala Thr Arg Ile Ser Phe Ser Arg Arg Arg Phe Ser Val Ser Val
1               5                   10                  15
Gly Arg (2) INFORMATION FOR SEQ ID NO:29:

(i) SEQUENCE CHARACTERISTICS:
(A) LENGTH: 18 amino acids
(B) TYPE: amino acid
(C) STRANDEDNESS: single
(D) TOPOLOGY: linear (ix) FEATURE:
(A) NAME/KEY: Modified-site
(B) LOCATION: 10
(D) OTHER INFORMATION: /product="homoarginine(Har)"

(xi) SEQUENCE DESCRIPTION: SEQ ID NO:29:

Arg Gly Gly Lys Val Cys Tyr Gly Arg Xaa Arg Phe Ser Val Cys Val
1               5                   10                  15
Gly Arg (2) INFORMATION FOR SEQ ID NO:30:

(i) SEQUENCE CHARACTERISTICS:
(A) LENGTH: 18 amino acids
(B) TYPE: amino acid
(C) STRANDEDNESS: single
(D) TOPOLOGY: linear (ix) FEATURE:
(A) NAME/KEY: Modified-site
(B) LOCATION: group(9, 18)
(D) OTHER INFORMATION: /note= "D form of amino acids"

(xi) SEQUENCE DESCRIPTION: SEQ ID NO:30:

Arg Ala Thr Arg Ile Val Phe Cys Arg Arg Arg Phe Gly Val Cys Val
1               5                   10                  15
Gly Arg (2) INFORMATION FOR SEQ ID NO:31:

(i) SEQUENCE CHARACTERISTICS:
(A) LENGTH: 18 amino acids
(B) TYPE: amino acid
(C) STRANDEDNESS: single
(D) TOPOLOGY: linear (ix) FEATURE:

-continued

```
( A ) NAME/KEY: Modified-site
( B ) LOCATION: 10
( D ) OTHER INFORMATION: /product="homoarginine(Har)"
      / note= "D form of amino acid"

( x i ) SEQUENCE DESCRIPTION: SEQ ID NO:31:

Arg Gly Gly Lys Val Cys Tyr Leu Arg Xaa Arg Phe Leu Val Cys Val
 1               5                  10                  15
Gly Arg
```

DNA SEQUENCES ENCODING PROTEGRINS AND PROTEGRIN ANALOGS AND THEIR USE IN RECOMBINANT METHODS OF PRODUCING PROTEGRINS

This is a Continuation-In-Part of U.S. Ser. No. 08/095, 769 filed 26 Jul. 1993 issued as U.S. Pat. No. 5,464,823, on Nov. 7, 1995 which is a Continuation-In-Part of U.S. Ser. No. 08/093,926 filed 20 Jul. 1993, now abandoned. The contents of these applications are incorporated herein by reference.

This invention was made with funding from NIH Grant No. A122839. The U.S. Government has certain rights in this invention.

TECHNICAL FIELD

The invention relates to the field of antibiotic peptides. In particular, the invention concerns short peptides, some of which are isolated from porcine leukocytes, that have a wide range of antimicrobial activities.

BACKGROUND ART

One of the defense mechanisms against infection by both animals and plants is the production of peptides that have antimicrobial and antiviral activity. Various classes of these peptides have been isolated from tissues both of plants and animals. One well known class of such peptides is the tachyplesins which were first isolated from the hemocytes of the horseshoe crab as described by Nakamura, T. et al. *J Biol Chem* (1988) 263:16709–16713. This article described the initial tachyplesin isolated from the Japanese species, Tachyplesin I, which is a 17-amino acid amidated peptide containing four cysteine residues providing two intramolecular cystine bonds. In a later article by this group, Miyata, T. et al. *J Biochem* (1989) 106:663–668, extends the studies to the American horseshoe crab and isolated a second tachyplesin, Tachyplesin II, consisting of 17 residues amidated at the C-terminus, also containing four cysteine residues and two intramolecular disulfide bonds. Two additional 18-mers, called polyphemusins, highly homologous to Tachyplesin II and containing the same positions for the four cysteine residues, were also isolated. Polyphemusin I and Polyphemusin II differ from each other only in the replacement of one arginine residue by a lysine. All of the peptides were described as having antifungal and antibacterial activity. A later article by Murakami, T. et al. *Chemotherapy* (1991) 37:327–334, describes the antiviral activity of the tachyplesins with respect to vesicular stomatus virus; Herpes Simplex Virus I & II, Adenovirus I, Reovirus II and Poliovirus I were resistant to inactivation by Tachyplesin I. Morimoto, M. et al. *Chemotherapy* (1991) 37:206–211, found that Tachyplesin I was inhibitory to Human Immunodeficiency Virus. This anti-HIV activity was found also to be possessed by a synthetic analog of Polyphemusin II as described by Nakashima, H. et al. *Antimicrobial Agents and Chemotherapy* (1992) 1249–1255. Antiviral peptides have also been found in rabbit leukocytes as reported by Lehrer, R.I. et al. *J Virol* (1985) 54:467–472.

Other important classes of cysteine-containing antimicrobial peptides include the defensins, β-defensins and insect defensins. The defensins are somewhat longer peptides characterized by six invariant cysteines and three intramolecular cystine disulfide bonds. Defensins were described by Lehrer, R.I. et al. *Cell* (1991) 64:229–230; Lehrer, R.I. et al. *Ann Rev Immunol* (1993) 11:105–128. A review of mammalian-derived defensins by Lehrer, R.I. et al. is found in *Annual Review Immunol* (1993) 11:105–128; three patents have issued on the defensins: U.S. Pat. No. 4,705,777; U.S. Pat. No. 4,659,692; and U.S. Pat. No. 4,543,252. Defensins have been found in the polymorphonucleated neutrophils (PMN) of humans and of several other animals, as well as in rabbit pulmonary alveolar macrophages, and in murine small intestinal epithelial (Paneth) cells and in corresponding cells in humans.

β-Defensins are found in bovine respiratory epithelial cells, bovine granulocytes and avian leukocytes. See Selsted, M.E. et al. *J Biol Chem* (1993) 288:6641–6648 and Diamond, G. et al. *Proc Natl Acad Sci* (USA) (1991) 88:3952–3958. Insect defensins have been reported by Lambert, J. et al. *Proc Natl Acad Sci* (USA) (1989) 88:262–265.

Antifungal and antibacterial peptides and proteins have also been found in plants (Broekaert, W.F. et al. *Biochemistry* (1992) 31:4308–4314) as reviewed by Cornelissen, B. J. C. et al. *Plant Physiol* (1993) 101:709–712. Expression systems for the production of such peptides have been used to transform plants to protect the plants against such infection as described, for example, by Haln, R. et al. *Nature* (1993) 361:153–156.

The present invention provides a new class of antimicrobial and antiviral peptides, designated "protegrins" herein, representative members of which have been isolated from porcine leukocytes. These peptides are useful as antibacterial antiviral and antifungal agents in both plants and animals.

The isolation of the protegrin peptides of the invention was reported by the present applicants in a paper by Kokryakov, V. N. et al. *FEBS* (1993) 337:231–236 (July issue). An additional paper disclosing cationic peptides from porcine neutrophils was published by Mirgorodskaya, O. A. et al. *FEBS* (1993) 330:339–342 (September issue). Storici, P. et al. *Biochem Biophys Res Comm* (1993) 196:1363–1367, report the recovery of a DNA sequence which encodes a pig leukocyte antimicrobial peptide with a cathelin-like prosequence. The peptide is reported to be one of the protegrins disclosed hereinbelow.

The protegrins of the invention have also been found to bind to endotoxins—i.e., the lipopolysaccharide (LPS) compositions derived from gram-negative bacteria which are believed responsible for gram-negative sepsis. This type of sepsis is an extremely common condition and is often fatal. Others have attempted to design and study proteins which bind LPS/endotoxin, and illustrative reports of these attempts appear in Rustici, A. et al. *Science* (1993) 259:361–364; Matsuzaki, K. et al. *Biochemistry* (1993) 32:11704–11710; Hoess, A. et al. *EMBO J* (1993) 12:3351–3356; and Elsbach, P. et al. *Current Opinion in Immunology* (1993) 5:103–107. The protegrins of the present invention provide additional compounds which are capable of inactivating of LPS and ameliorating its effects.

DISCLOSURE OF THE INVENTION

In one embodiment, the invention is directed to peptides of 16–18 amino acid residues characterized by four invariant cysteines and either by a characteristic pattern of basic and hydrophobic amino acids and/or being isolatable from animal leukocytes using the method of the invention. In a second embodiment, the invention is directed to the above peptides wherein 1–4 of these cysteines is replaced by a hydrophobic or small amino acid. These peptides can be produced synthetically and some can be produced recombinantly or can be isolated from their native sources and purified for use as preservatives or in pharmaceutical compositions in treating or preventing infection in animals. Alternatively, the peptides can be formulated into compositions which can be applied to plants to protect them against viral or microbial infection. In still another approach, the DNA encoding the peptides can be expressed in situ, in animals or preferably in plants, to combat infections. The peptides are also useful as standards in antimicrobial assays and in binding endotoxins Accordingly, in one aspect, the invention is directed to peptides of the formula:

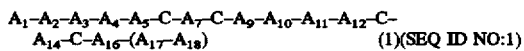
(1)(SEQ ID NO:1)

and the amidated or esterified and/or N-terminal acylated forms thereof, including the optionally SH-stabilized linear and the cyclic forms thereof or the modified forms thereof wherein $A_1$, $A_9$, $A_{10}$ and All are basic amino acids;
$A_2$ and $A_3$ are small amino acids;
$A_5$, $A_7$, $A_{12}$, $A_{14}$ and $A_{16}$ are hydrophobic amino acids;
$A_4$ is a basic or a small amino acid;
$A_{17}$ is either not present or is a small amino acid; and
$A_{18}$ is not present if $A_{17}$ is not present or, if $A_{17}$ is present, A18 may be not present or is a basic amino acid, and wherein said modified forms are compounds of Formula (1) which have been modified by replacing one or more of the cysteines with a small amino acid or a hydrophobic amino acid.

In another aspect, the invention comprises a purified and isolated peptide of the formula:

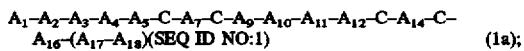
(1a);

and the amidated or esterified and/or N-terminal acylated forms thereof, including the optionally SH-stabilized linear and the cyclic forms thereof wherein $A_{1-5}$, $A_7$, $A_{9-12}$ and $A_{14}$ and $A_{16}$, and, if present, $A_{17}$ and $A_{18}$ (i.e. $A_n$), represent amino acid residues which peptides are isolatable from animal leukocytes by the methods similar to those described herein.

In still other aspects, the invention is directed to recombinant materials useful for the production of the peptides of the invention as well as plants or animals modified to contain expression systems for the production of these peptides. The invention is also directed to pharmaceutical compositions and compositions for application to plants containing the peptides of the invention as active ingredients or compositions which contain expression systems for production of the peptides or for in situ expression of the nucleotide sequence encoding these peptides. The invention is also directed to methods to prepare the invention peptides synthetically, to antibodies specific for these peptides, and to the use of the peptides as preservatives.

In other aspects, the invention is directed to the use of the compounds of the invention as standards in antimicrobial assays, and as antimicrobial compounds in solutions useful in eye care, such as contact lens solutions. The invention is also directed to use of the invention compounds as preservatives for foods or other perishables. As the invention peptides can inactivate endotoxin, the invention is also directed to a method to inactivate endotoxins using the compounds of the invention and to treat gram-negative sepsis by taking advantage of this property.

BRIEF DESCRIPTION OF THE DRAWINGS

FIG. 4 shows the antimicrobial activity of the purified porcine protegrins of the invention:

FIG. 5 shows the effect of various test conditions on antimicrobial activity:

FIG. 6 shows the antimicrobial activity of the linear forms of the protegrins under various test conditions:

MODES OF CARRYING OUT THE INVENTION

Figure 1:
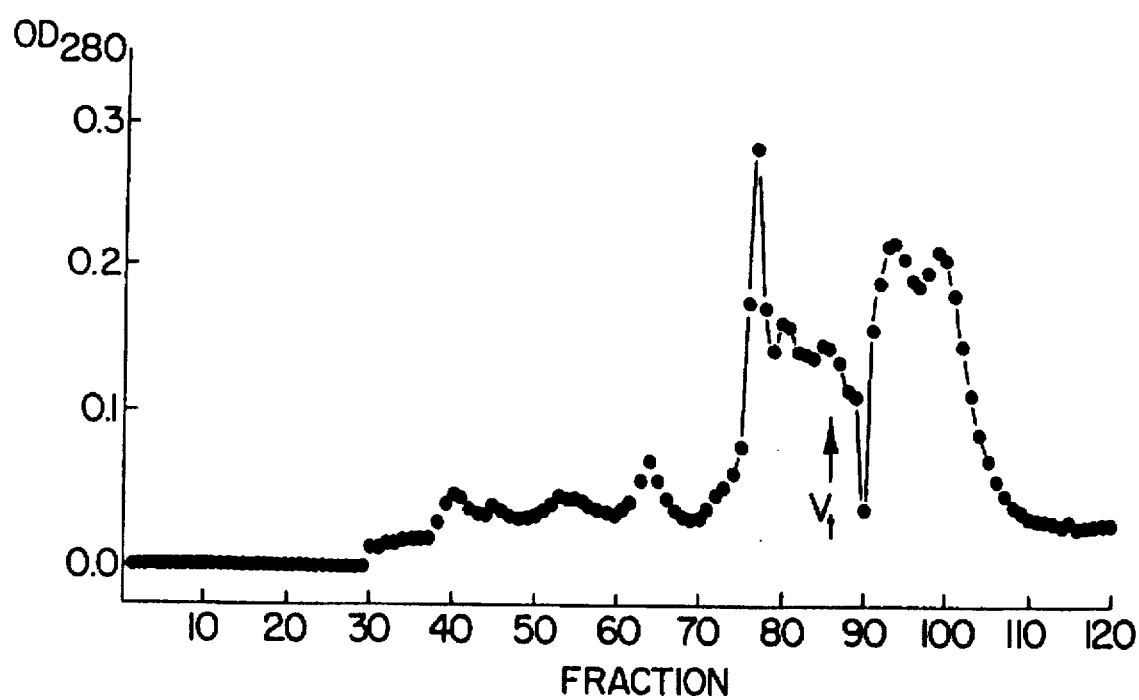
FIG. 1 shows the elution pattern of a concentrate of the ultrafiltrate of porcine leukocytes applied to a Biogel P10 column.

The peptides of the invention are described by the formula:

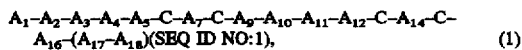
(1)

and its defined modified forms. Those peptides which occur in nature must be in purified and isolated form.

The designation $A_n$ in each case represents an amino acid at the specified position in the peptide. As $A_{17}$ and $A_{18}$ may or may not be present, the peptides of the invention contain either 16, 17 or 18 amino acids. The positions of the cysteine residues, shown as C in Formula (1), are invariant in the peptides of the invention; however, in the modified forms of the peptides of Formula (1), also included within the scope of the invention, 1–4 of these cysteines may be replaced by a hydrophobic or small amino acid.

The amino terminus of the peptide may be in the free amino form or may be acylated by a group of the formula RCO—, wherein R represents a hydrocarbyl group of 1–6C. The hydrocarbyl group is saturated or unsaturated and is typically, for example, methyl, ethyl, i-propyl, t-butyl, n-pentyl, cyclohexyl, cyclohexene-2-yl, hexene-3-yl, hexyne-4-yl, and the like.

The C-terminus of the peptides of the invention may be in the form of the underivatized carboxyl group, either as the free acid or an acceptable salt, such as the potassium, sodium, calcium, magnesium, or other salt of an inorganic ion or of an organic ion such as caffeine. The carboxyl terminus may also be derivatized by formation of an ester with an alcohol of the formula ROH, or may be amidated by an amine of the formula $NH_3$, or $RNH_2$, or $R_2NH$, wherein each R is independently hydrocarbyl of 1–6C as defined above. Amidated forms of the peptides wherein the C-terminus has the formula $CONH_2$ are preferred.

As the peptides of the invention contain substantial numbers of basic amino acids, the peptides of the invention may be supplied in the form of the acid addition salts. Typical acid addition salts include those of inorganic ions such as chloride, bromide, iodide, fluoride or the like, sulfate, nitrate, or phosphate, or may be salts of organic anions such as acetate, formate, benzoate and the like. The acceptability of each of such salts is dependent on the intended use, as is commonly understood.

The peptides of the invention that contain at least two cysteines may be in straight-chain or cyclic form. The straight-chain forms are convertible to the cyclic forms, and vice versa. Methods for forming disulfide bonds to create the cyclic peptides are well known in the art, as are methods to reduce disulfides to form the linear compounds. The linear compounds can be stabilized by addition of a suitable alkylating agent such as iodoacetamide.

The cyclic forms are the result of the formation of cystine linkages among all or some of the four invariant cysteine residues. Cyclic forms of the invention include all possible permutations of cystine bond formation; if the cysteines are numbered in order of their occurrence starting at the N-terminus as $C_1$, $C_2$, $C_3$ and $C_4$, these permutations include:

$C_1$–$C_2$;
$C_1$–$C_3$;
$C_1$–$C_4$;
$C_2$–$C_3$;
$C_2$–$C_4$;
$C_3$–$C_4$;
$C_1$–$C_2$, $C_3$–$C_4$;
$C_1$–$C_3$, $C_2$–$C_4$; and
$C_1$–$C_4$, $C_2$–$C_3$.

In the modified forms of the peptides, where 1–4 cysteines are replaced, similar permutations are available when 2–3 cysteines are present.

As the linearalized forms of the native cyclic peptides have valuable activities, even when stabilized to preserve the sulfhydryl form of cysteine, for example, by reaction with iodoacetamide, the compounds of the invention also include linearalized forms which are stabilized with suitable reagents. As defined herein, "SH-stabilized" forms of the peptides of the invention contain sulfhydryl groups reacted with standard reagents to prevent reformation into disulfide linkages.

The amino acids denoted by $A_n$ may be those encoded by the gene or analogs thereof, and may also be the D-isomers thereof. One preferred embodiment of the peptides of the invention is that form wherein all of the residues are in the D-configuration thus conferring resistance to protease activity while retaining antimicrobial or antiviral properties. The amino acid notations used herein are conventional and are as follows:

| Amino Acid | One-Letter Symbol | Three-letter Symbol |
|---|---|---|
| Alanine | A | Ala |
| Arginine | R | Arg |
| Asparagine | N | Asn |
| Aspartic acid | D | Asp |
| Cysteine | C | Cys |
| Glutamine | Q | Gln |
| Glutamic acid | E | Glu |
| Glycine | G | Gly |
| Histidine | H | His |
| Isoleucine | I | Ile |
| Leucine | L | Leu |
| Lysine | K | Lys |
| Methionine | M | Met |
| Phenylalanine | F | Phe |
| Proline | P | Pro |
| Serine | S | Ser |
| Threonine | T | Thr |
| Tryptophan | W | Trp |
| Tyrosine | Y | Tyr |
| Valine | V | Val |

The amino acids not encoded genetically are abbreviated as indicated in the discussion below.

In the specific peptides shown in the present application, the L-form of any amino acid residue having an optical isomer is intended unless the D-form is expressly indicated by a dagger superscript ($\dagger$).

The compounds of the invention are peptides which are partially defined in terms of amino acid residues of designated classes. Amino acid residues can be generally subclassified into major subclasses as follows:

Acidic: The residue has a negative charge due to loss of H ion at physiological pH and the residue is attracted by aqueous solution so as to seek the surface positions in the conformation of a peptide in which it is contained when the peptide is in aqueous medium at physiological pH.

Basic: The residue has a positive charge due to association with H ion at physiological pH and the residue is attracted by aqueous solution so as to seek the surface positions in the conformation of a peptide in which it is contained when the peptide is in aqueous medium at physiological pH.

Hydrophobic: The residues are not charged at physiological pH and the residue is repelled by aqueous solution so as to seek the inner positions in the conformation of a peptide in which it is contained when the peptide is in aqueous medium.

Neutral/polar: The residues are not charged at physiological pH, but the residue is not sufficiently repelled by aqueous solutions so that it would seek inner positions in the conformation of a peptide in which it is contained when the peptide is in aqueous medium.

This description also characterizes certain amino acids as "small" since their side chains are not sufficiently large, even if polar groups are lacking, to confer hydrophobicity. "Small" amino acids are those with four carbons or less when at least one polar group is on the side chain and three carbons or less when not.

It is understood, of course, that in a statistical collection of individual residue molecules some molecules will be charged, and some not, and there will be an attraction for or repulsion from an aqueous medium to a greater or lesser extent. To fit the definition of "charged," a significant percentage (at least approximately 25%) of the individual molecules are charged at physiological pH. The degree of attraction or repulsion required for classification as polar or nonpolar is arbitrary and, therefore, amino acids specifically contemplated by the invention have been classified as one or the other. Most amino acids not specifically named can be classified on the basis of known behavior.

Amino acid residues can be further subclassified as cyclic or noncyclic, and aromatic or nonaromatic, self-explanatory classifications with respect to the side-chain substituent groups of the residues, and as small or large. The residue is considered small if it contains a total of four carbon atoms or less, inclusive of the carboxyl carbon, provided an additional polar substituent is present; three or less if not. Small residues are, of course, always nonaromatic.

For the naturally occurring protein amino acids, subclassification according to the foregoing scheme is as follows.

Acidic: Aspartic acid and Glutamic acid;
Basic:
  Noncyclic: Arginine, Lysine;
  Cyclic: Histidine;
Small: Glycine, Serine, Alanine, Threonine;
Polar/large: Asparagine, Glutamine;
Hydrophobic: Tyrosine, Valine, Isoleucine, Leucine, Methionine, Phenylalanine, Tryptophan.

The gene-encoded secondary amino acid proline is a special case due to its known effects on the secondary conformation of peptide chains, and is not, therefore, included in a group. Cysteine residues are also not included in these classifications since their capacity to form disulfide bonds to provide secondary structure is critical in the compounds of the present invention.

Certain commonly encountered amino acids, which are not encoded by the genetic code, include, for example, beta-alanine (beta-Ala), or other omega-amino acids, such as 3-aminopropionic, 2,3-diaminopropionic (2,3-diaP), 4-aminobutyric and so forth, alpha-aminisobutyric acid (Aib), sarcosine (Sar), ornithine (Orn), citrulline (Cit), t-butylalanine (t-BuA), t-butylglycine (t-BuG), N-methylisoleucine (N-MeIle), phenylglycine (Phg), and cyclohexylalanine (Cha), norleucine (Nle), 2-naphthylalanine (2-Nal); 1,2,3,4-tetrahydroisoquinoline-3-carboxylic acid (Tic); β-2-thienylalanine (Thi); methionine sulfoxide (MSO); and homoarginine (Har). These also fall conveniently into particular categories.

Based on the above definitions,
Sar, beta-Ala, 2,3-diaP and Aib are small;
t-BuA, t-BuG, N-MeIle, Nle, Mvl, Cha, Phg, Nal, Thi and Tic are hydrophobic;
Orn and Har are basic;
Cit, Acetyl Lys, and MSO are neutral/polar.

The various omega-amino acids are classified according to size as small (beta-Ala and 3-aminopropionic) or large and hydrophobic (all others).

Other amino acid substitutions of those encoded in the gene can also be included in peptide compounds within the scope of the invention and can be classified within this general scheme according to their structure.

In all of the peptides of the invention, one or more amide linkages (—CO—NH—) may optionally be replaced with another linkage which is an isostere such as —CH$_2$NH—, —CH$_2$S—, —CH$_2$CH$_2$, —CH=CH—(cis and trans), —COCH$_2$—, —CH(OH) CH$_2$— and —CH$_2$SO—. This replacement can be made by methods known in the art. The following references describe preparation of peptide analogs which include these alternative-linking moieties: Spatola, A. F., *Vega Data* (March 1983), Vol. 1, Issue 3, "Peptide Backbone Modifications" (general review); Spatola, A. F., in "Chemistry and Biochemistry of Amino Acids Peptides and Proteins," B. Weinstein, eds., Marcel Dekker, New York, p. 267 (1983) (general review); Morley, J. S., *Trends Pharm Sci* (1980) pp. 463–468 (general review); Hudson, D., et al., *Int J Pept Prot Res* (1979) 14:177–185 (—CH$_2$NH—, —CH$_2$CH$_2$—); Spatola, A. F., et al., *Life Sci* (1986) 38:1243–1249 (—CH$_2$—S); Harm, M. M., *J Chem Soc Perkin Trans I* (1982) 307–314 (—CH—CH—, cis and trans); Almquist, R. G., et al., *J Med Chem* (1980) 23:1392–1398 (—COCH$_2$—); jennings-White, C., et al., *Tetrahedron Lett* (1982) 23:2533 (—COCH$_2$—); Szelke, M., et al., European Application EP 45665 (1982) CA:97:39405 (1982) (—CH(OH) CH$_2$—); Holladay, M. W., et al., *Tetrahedron Lett* (1983) 24:4401–4404 (—(OH)CH$_2$—); and Hruby, V. J., *Life Sci* (1982) 31:189–199 (—CH$_2$—S—).

The compounds of Formula (1)(SEQ ID NO: 1) are defined as follows:

$A_1$, $A_9$, $A_{10}$ and $A_{11}$ are basic amino acids;
$A_2$ and $A_3$ are small amino acids;
$A_5$, $A_7$, $A_{12}$, $A_{14}$ and $A_{16}$ are hydrophobic amino acids;
$A_4$ is a basic or a small amino acid;
$A_{17}$ is either not present or is a small amino acid; and
$A_{18}$ is not present if $A_{17}$ is not present or, if $A_{17}$ is present, $A_{18}$ may be not present or is a basic amino acid.

In preferred embodiments of the compounds of the invention, $A_1$, $A_9$, $A_{10}$ and $A_{11}$ are selected from the group consisting of R, K and Har; more preferably, all of $A_1$, $A_9$, $A_{10}$ and $A_{11}$ are R.

In another class of preferred embodiments, $A_2$ and $A_3$ are selected from the group consisting of G, A, S and T; more preferably, $A_1$ and $A_2$ are G.

In another set of preferred embodiments, $A_4$ is selected from the group consisting of R, K, Har, G, A, S and T; more preferably, $A_4$ is R or G.

In another set of preferred embodiments, $A_5$, $A_{14}$ and $A_{16}$ are selected independently from the group consisting of I, V and L and Nle; preferably I, V and L.

In another set of preferred embodiments, $A_7$ and $A_{12}$ are selected from the group consisting of W, Y and F; preferably $A_7$ is Y and $A_{12}$ is F.

$A_{17}$, when present, is preferably G, A, S or T, most preferably G;

$A_{18}$, when present, is preferably R, K or Har, most preferably R.

As described above, the compounds of Formula (1) are either in cyclic or noncyclic (linearalized) form or may be modified wherein 1–4 of the cysteines is replaced by a small amino acid residue or a basic amino acid residue. If the linearalized forms of the compound of Formula (1) are prepared, or if linearalized forms of those modified peptides which contain at least two cysteines are prepared, it is preferred that the sulfhydryl groups be stabilized by addition of a suitable reagent. Preferred embodiments for the hydrophobic amino acid to replace cysteine residues are I, V, L and NLi, preferably I, V or L. Preferred small amino acids to replace the cysteine residues include G, A, S and T, most preferably G.

In an alternative embodiment, the peptides of the invention are defined as described by Formula (1) (SEQ ID NO: 1), but wherein the definitions of $A_n$ in each case are determined by the isolatability of the peptide from animal leukocytes by the invention method. The invention method comprises the steps of providing an ultrafiltrate of a lysate of animal leukocytes and isolating peptides of 16–18 amino acids. These peptides can further be defined by the ability of DNA encoding them to hybridize under stringent conditions to DNA encoding the peptides exemplified as PG-1, PG-2, and PG-3 herein.

Particularly preferred compounds of the invention are:

| Unmodified forms |
|---|
| PG-1: R—G—G—R—L—C—Y—C—R—R—R—F—C—V—C—V—G—R (SEQ ID NO: 2) |
| PG-2: R—G—G—R—L—C—Y—C—R—R—R—F—C—I—C—V (SEQ ID NO: 3) |
| PG-3: R—G—G—G—L—C—Y—C—R—R—R—F—C—V—C—V—G—R (SEQ ID NO: 4) |
| R—G—G—R—L—C—Y—C—R—R—R—F—C—V—C—V (SEQ ID NO: 5) |
| K—G—G—R—L—C—Y—C—R—R—R—F—C—V—C—V (SEQ ID NO: 6) |
| R—G—G—Har—L—C—Y—C—R—R—R—F—C—V—C—V (SEQ ID NO: 7) |
| R—G—G—Har—L—C—Y—C—Har—R—R—F—C—V—C—V—G—R (SEQ ID NO: 8) |
| R—G—G—R—V—C—Y—C—R—Har—R—F—C—V—C—V—G—R (SEQ ID NO: 9) |
| R—G—G—R—L—C—Y—C—R—K—K—W—C—V—C—V—G—R (SEQ ID NO: 10) |
| R—G—G—R—L—C—Y—C—R—Har—R—Y—C—V—C—V—G—R (SEQ ID NO: 11) |
| R—G—S—G—L—C—Y—C—R—R—K—W—C—V—C—V—G—R (SEQ ID NO: 12) |
| R—A—T—R—I—C—F—C—R—R—R—F—C—V—C—V—G—R (SEQ ID NO: 13) |
| R—G—G—K—V—C—Y—C—R—Har—R—F—C—V—C—V—G—R (SEQ ID NO: 14) |
| R—A—T—R—I—C—F—C—R†—R—R—F—C—V—C—V—G—R† (SEQ ID NO: 15) |
| R—G—G—K—V—C—Y—C—R—Har†—R—F—C—V—C—V—G—R (SEQ ID NO: 16) | both the linear and cyclic forms thereof, and including the N-terminal acylated and C-terminal amidated forms;

| Modified forms |
|---|
| R—G—G—R—L—V—Y—C—R—R—R—F—C—V—C—V—G—R (SEQ ID NO: 17) |
| R—G—G—R—L—G—Y—C—R—R—R—F—C—I—C—V (SEQ ID NO: 18) |
| R—G—G—G—L—C—Y—G—R—R—R—F—C—V—C—V—G—R (SEQ ID NO: 19) |
| R—G—G—R—L—G—Y—G—R—R—R—F—G—V—C—V (SEQ ID NO: 20) |
| K—G—G—R—L—V—Y—V—R—R—R—F—I—V—C—V (SEQ ID NO: 21) |
| R—G—G—Har—L—C—Y—C—R—R—R—F—C—V—G—V (SEQ ID NO: 22) |
| R—G—G—Har—L—C—Y—C—Har—R—R—F—C—V—L—V—G—R (SEQ ID NO: 23) |
| R—G—G—R—V—C—Y—V—R—Har—R—F—L—V—G—V—G—R (SEQ ID NO: 24) |
| R—G—G—R—L—C—Y—S—R—K—K—W—C—V—S—V—G—R (SEQ ID NO: 25) |
| R—G—G—R—L—C—Y—C—R—Har—R—Y—S—V—V—V—G—R (SEQ ID NO: 26) |
| R—G—S—G—L—S—Y—C—R—R—K—W—G—V—C—V—G—R (SEQ ID NO: 27) |
| R—A—T—R—I—S—F—S—R—R—R—F—S—V—S—V—G—R (SEQ ID NO: 28) |
| R—G—G—K—V—C—Y—G—R—Har—R—F—S—V—C—V—G—R (SEQ ID NO: 29) |
| R—A—T—R—I—V—F—C—R†—R—R—F—G—V—C—V—G—R† (SEQ ID NO: 30) |
| R—G—G—K—V—C—Y—L—R—Har†—R—F—L—V—C—V—G—R (SEQ ID NO: 31) | both the linear and cyclic (where possible) forms thereof, and including the N-terminal acylated and C-terminal amidated forms.

Preparation of the Invention Compounds

The invention compounds, often designated herein "protegrins" are essentially peptide backbones which may be modified at the N- or C-terminus and also may contain one or two cystine disulfide linkages. The peptides may first be synthesized in noncyclized form. These peptides may then be converted to the cyclic peptides if desired by standard methods of cystine bond formation. As applied to the protegrins herein, "cyclic forms" refers to those forms which contain cyclic portions by virtue of the formation of disulfide linkages between cysteine residues in the peptide. If the straight-chain forms are preferred, it is preferable to stabilize the sulfhydryl groups for any peptides of the invention which contain two or more cysteine residues.

Standard methods of synthesis of peptides the size of protegrins are known. Most commonly used currently are solid phase synthesis techniques; indeed, automated equipment for systematically constructing peptide chains can be purchased. Solution phase synthesis can also be used but is considerably less convenient. When synthesized using these standard techniques, amino acids not encoded by the gene and D-enantiomers can be employed in the synthesis. Thus, one very practical way to obtain the compounds of the invention is to employ these standard chemical synthesis techniques.

In addition to providing the peptide backbone, the N- and/or C-terminus can be derivatized, again using conventional chemical techniques. The compounds of the invention may optionally contain an acyl group, preferably an acetyl group at the amino terminus. Methods for acetylating or, more generally, acylating, the free amino group at the N-terminus are generally known in the art; in addition, the N-terminal amino acid may be supplied in the synthesis in acylated form.

At the carboxy terminus, the carboxyl group may, of course, be present in the form of a salt; in the case of pharmaceutical compositions this will be a pharmaceutically acceptable salt. Suitable salts include those formed with inorganic ions such as $NH_4^+$, $Na^+$, $K^+$, $Mg^{++}$, $Ca^{++}$, and the like as well as salts formed with organic cations such as those of caffeine and other highly substituted amines. The carboxy terminus may also be esterified using alcohols of the formula ROH wherein R is hydrocarbyl (1–6C) as defined above. Similarly, the carboxy terminus may be amidated so as to have the formula —$CONH_2$, —CONHR, or -$CONR_2$, wherein each R is independently hydrocarbyl (1–6C) as herein defined. Techniques for esterification and amidation as well as neutralizing in the presence of base to form salts are all standard organic chemical techniques.

If the peptides of the invention are prepared under physiological conditions, the side-chain amino groups of the basic amino acids will be in the form of the relevant acid addition salts.

Formation of disulfide linkages, if desired, is conducted in the presence of mild oxidizing agents. Chemical oxidizing agents may be used, or the compounds may simply be exposed to the oxygen of the air to effect these linkages.

If the peptide backbone is comprised entirely of gene-encoded amino acids, or if some portion of it is so composed, the peptide or the relevant portion may also be synthesized using recombinant DNA techniques. The DNA encoding the peptides of the invention may itself be synthesized using commercially available equipment; codon choice can be integrated into the synthesis depending on the nature of the host. Alternatively, although less convenient, the DNA can be obtained, at least initially, by screening a cDNA library prepared from porcine leukocytes using probes or PCR primers based on the sequences of the protegrins described herein. This results in recovery of the naturally occurring sequence encoding the protegrins of the invention. Obtention of this native sequence is significant for purposes other than the synthesis of the protegrins per se; the availability of the naturally occurring sequences provides a useful probe to obtain corresponding DNA encoding protegrins of other species. Thus, cDNA libraries, for example, of leukocytes derived from other animals can be screened using the native DNA, preferably under conditions of high stringency. High stringency is as defined by Maniatis, et al. *Molecular Cloning: a Laboratory Manual* 2nd Ed, Cold Spring Harbor Laboratory Press (1989), the relevant portions of which are incorporated herein by reference. This procedure also permits recovery of allelic variants of these peptides from the same species.

Alternatively, the protegrins can be prepared by isolation from leukocytes of a desired species using techniques similar to those disclosed herein for the isolation of porcine protegrins. In general, these techniques involve preparing a lysate of a leukocyte preparation, ultrafiltering the supernatant of the clarified lysate and recovering the ultrafiltrate. The ultrafiltrate is then subjected to chromatographic separation. The location of fragments having antimicrobial and antiviral activity corresponding to protegrins can be assessed using criteria of molecular weight and assaying the fractions for the desired activities as described herein. The native forms of these peptides are believed to be the cyclic forms; if desired, the linearalized forms can be prepared by treating the peptides with reducing agents and stabilizing the sulfhydryl groups that result.

Isolated and recombinantly produced forms of the protegrins may require subsequent derivatization to modify the N- and/or C-terminus and, depending on the isolation procedure, to effect the formation of cystine bonds as described hereinabove. Depending on the host organism used for recombinant production and the animal source from which the protein is isolated, some or all of these conversions may already have been effected.

For recombinant production, the DNA encoding the protegrins of the invention is included in an expression system which places these coding sequences under control of a suitable promoter and other control sequences compatible with an intended host cell. Types of host cells available span almost the entire range of the plant and animal kingdoms. Thus, the protegrins of the invention could be produced in bacteria or yeast (to the extent that they can be produced in a nontoxic or refractile form or utilize resistant strains) as well as in animal cells, insect cells and plant cells. Indeed, modified plant cells can be used to regenerate plants containing the relevant expression systems so that the resulting transgenic plant is capable of self protection vis-à-vis these infective agents.

The protegrins of the invention can be produced in a form that will result in their secretion from the host cell by fusing to the DNA encoding the protegrin, a DNA encoding a suitable signal peptide, or may be produced intracellularly. They may also be produced as fusion proteins with additional amino acid sequence which may or may not need to be subsequently removed prior to the use of these compounds as antimicrobials or antivirals.

Thus, the protegrins of the invention can be produced in a variety of modalities including chemical synthesis, recombinant production, isolation from natural sources, or some combination of these techniques.

Those members of the protegrin class which occur naturally are supplied in purified and isolated form. By "purified and isolated" is meant free from the environment in which the peptide normally occurs (in the case of such naturally occurring peptides) and in a form where it can be used practically. Thus, "purified and isolated" form means that the peptide is substantially pure, i.e., more than 90% pure, preferably more than 95% pure and more preferably more than 99% pure or is in a completely different context such as that of a pharmaceutical preparation.

Antibodies

Antibodies to the protegrins of the invention may also be produced using standard immunological techniques for production of polyclonal antisera and, if desired, immortalizing the antibody-producing cells of the immunized host for sources of monoclonal antibody production. Techniques for producing antibodies to any substance of interest are well known. It may be necessary to enhance the immunogenicity of the substance, particularly as here, where the material is only a short peptide, by coupling the hapten to a carrier. Suitable carriers for this purpose include substances which do not themselves produce an immune response in the mammal to be administered the hapten-carrier conjugate. Common carriers used include keyhole limpet hemocyanin (KLH), diphtheria toxoid, serum albumin, and the viral coat protein of rotavirus, VP6. Coupling of the hapten to the carrier is effected by standard techniques such as contacting the carrier with the peptide in the presence of a dehydrating agent such as dicyclohexylcarbodiimide or through the use of linkers such as those available through Pierce Chemical Company, Chicago, Ill.

The protegrins of the invention in immunogenic form are then injected into a suitable mammalian host and antibody titers in the serum are monitored. Polyclonal antisera may be harvested when titers are sufficiently high. Alternatively, antibody-producing cells of the host such as spleen cells or peripheral blood lymphocytes may be harvested and immortalized. The immortalized cells are then cloned as individual colonies and screened for the production of the desired monoclonal antibodies.

The antibodies of the invention are, of course, useful in immunoassays for determining the amount or presence of the protegrins. Such assays are essential in quality controlled production of compositions containing the protegrins of the invention. In addition, the antibodies can be used to assess the efficacy of recombinant production of the protegrins, as well as screening expression libraries for the presence of protegrin encoding genes.

Compositions Containing the Protegrins and Methods of Use

The protegrins of the invention are effective in inactivating a wide range of microbial and viral targets, including gram-positive and gram-negative bacteria, yeast, and certain strains of virus. Accordingly, they can be used in disinfectant compositions and as preservatives for materials such as foodstuffs, cosmetics, medicaments, or other materials containing nutrients for organisms. For use in such contexts, the protegrins are supplied either as a single protegrin, in admixture with several other protegrins, or in admixture with additional antimicrobial agents. In general, as these are preservatives in this context, they are usually present in relatively low amounts, of less than 5%, by weight of the total composition, more preferably less than 1%, still more preferably less than 0.1%.

The peptides of the invention are also useful as standards in antimicrobial assays and in assays for determination of capability of test compounds to bind to endotoxins such as lipopolysaccharides.

For use as antimicrobials or antivirals for treatment of animal subjects, the protegrins of the invention can be formulated as pharmaceutical or veterinary compositions. Depending on the subject to be treated, the mode of administration, and the type of treatment desired—e.g., prevention, prophylaxis, therapy; the protegrins are formulated in ways consonant with these parameters. A summary of such techniques is found in Remington's *Pharmaceutical Sciences*, latest edition, Mack Publishing Co., Easton, Pa.

The protegrins of the invention can be administered singly or as mixtures of several protegrins or in combination with other pharmaceutically active components. The formulations may be prepared in a manner suitable for systemic administration or topical or local administration. Systemic formulations include those designed for injection (e.g., intramuscular, intravenous or subcutaneous injection) or may be prepared for transdermal, transmucosal, or oral administration. The formulation will generally include a diluent as well as, in some cases, adjuvants, buffers, preservatives and the like. The protegrins can be administered also in liposomal compositions or as microemulsions.

If administration is to be oral, the protegrins of the invention must be protected from degradation in the stomach using a suitable enteric coating. This may be avoided to some extent by utilizing amino acids in the D-configuration, thus providing resistance to proteases. However, the peptide is still susceptible to hydrolysis due to the acidic conditions of the stomach; thus, some degree of enteric coating may still be required.

As described in the examples below, the peptides of the invention retain their activity against microbes in the context of borate solutions that are commonly used in eye care products. It has also been shown that when tested for antimicrobial activity against *E. coli* in the presence and absence of lysozyme in borate buffered saline, that the presence of lysozyme enhanced the effectiveness of PG-3. This effect was more pronounced when the PG-3 was autoclaved and similar patterns were obtained for both the free-acid form and the amide. Accordingly, the protegrins may be used as preservatives in such compositions or as antimicrobials for treatment of eye infections.

The protegrins of the invention may also be applied to plants or to their environment to prevent viral- and microbial-induced diseases in these plants. Suitable compositions for this use will typically contain a diluent as well as a spreading agent or other ancillary agreements beneficial to the plant or to the environment.

Thus, the protegrins of the invention may be used in any context wherein an antimicrobial and/or antiviral action is required. This use may be an entirely in vitro use, or the peptides may be administered to organisms.

In addition, the antimicrobial or antiviral activity may be generated in situ by administering an expression system suitable for the production of the protegrins of the invention.

Such expression systems can be supplied to plant and animal subjects using known techniques. For example, in animals, pox-based expression vectors can be used to generate the peptides in situ. Similarly, plant cells can be transformed with expression vectors and then regenerated into whole plants which are capable of their own production of the peptides.

A particularly useful property of the protegrins is their activity in the presence of serum. Unlike defensins, protegrins are capable of exerting their antimicrobial effects in the presence of serum.

As shown hereinbelow, the protegrins are capable of inactivating endotoxins derived from gram-negative bacteria—i.e., lipopolysaccharides (LPS)—in standard assays. Accordingly, the protegrins may be used under any circumstances where inactivation of LPS is desired. One such situation is in the treatment or amelioration of gram-negative sepsis.

The following examples are intended to illustrate but not to limit the invention.

EXAMPLE 1

Isolation of PG-1, PG-2 and PG-3

Fresh porcine blood was collected into 15-liter vessels containing 5% EDTA in normal saline, pH 7.4 as an anticoagulant (33 ml/liter blood). The blood cells were allowed to sediment for 90 minutes at room temperature and the leukocyte-rich supernatant was removed and centrifuged at 200 × g for 5.7 minutes. The pellets were pooled and suspended in 0.84% ammonium chloride to lyse erythrocytes and the resulting leukocytes (70–75% PMN, 5–10% eosinophils, 15–25% lymphocytes and monocytes) were washed in normal saline, resuspended in ice-cold 10% acetic acid at $10^8$/ml, homogenized and stirred overnight at 4° C. The preparation was centrifuged at 25,000 × g for 3 hours at 4° C. and the supernatant was lyophilized and weighed.

950 mg (dry weight) of lyophilized extract, which contained 520 mg protein by BCA analysis, was stirred overnight at 4° C. in 100 ml of 10% acetic acid and then centrifuged at 25,000 × g for 2 hours. The supernate was removed and passed by pressure through a 50 ml stirred ultracentrifugation cell (Amicon, Danvers Mass.) that contained a YM-5 filter. The ultrafiltrate (24.5 mg protein by BCA) was concentrated to 3 ml by vacuum centrifugation (SpeedVac Concentrator, Savant Instruments, Hicksville, N.Y.), applied to a 2.5×117 cm BioGel P10 column (Bio-Rad, Hercules, Calif.) and eluted at 4° C. with 5% acetic acid.

Fractions containing 6.6 ml were obtained. Fractions were assayed by absorption at 280 nm and the elution pattern is shown in FIG. 1.

Figure 2:
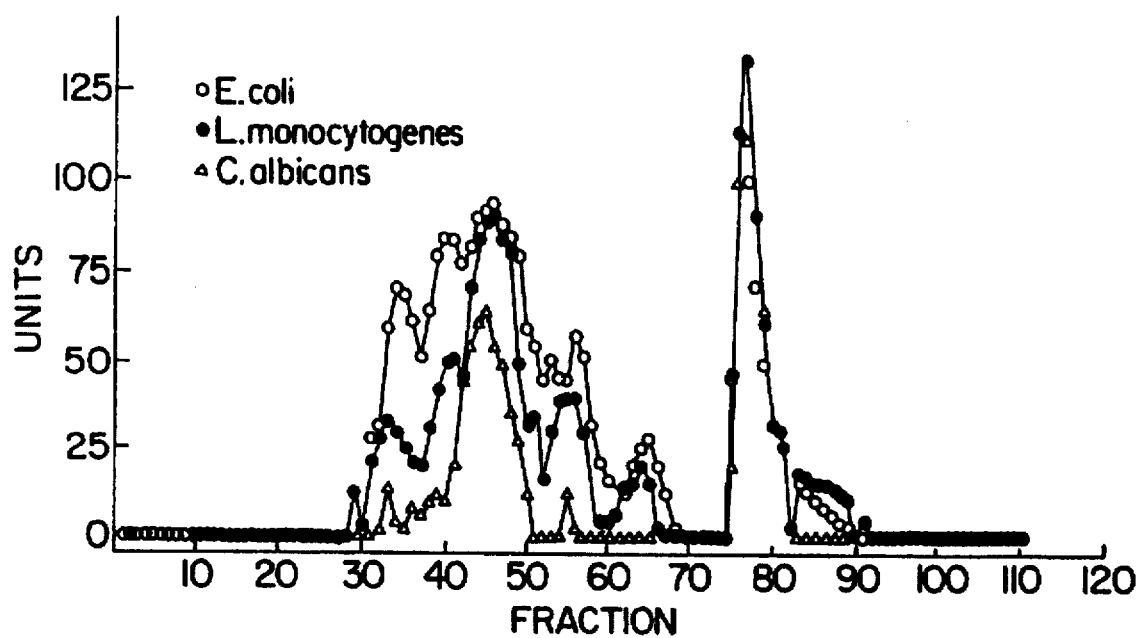
FIG. 2 shows the antibacterial activity of the P10 fractions obtained from elution of the column described in FIG. 1.

Aliquots (66 µl) of each fraction were dried by vacuum centrifugation and resuspended in 6.6 µl of 0.01% acetic acid. Five µl samples of this concentrate were tested for antimicrobial activity against *E. coli* ML-35, *L. monocytogenes*, strain EGD and *C. albicans*, strain 820, using radiodiffusion and gel overlay techniques as described by Lehrer, R. I. et al. *J Immunol Meth* (1991) 137:167–173. Briefly, the underlay agars used for all organisms had a final pH of 6.5 and contained 9 mM sodium phosphate/1 mM sodium citrate buffer, 1% w/v agarose and 0.30 mg/ml tryptocase soy broth powder (BBL Cockeysville, Md.). The units of activity in the radial diffusion assay were measured as described; 10 units correspond to a 1 mm diameter clear zone around the sample well. Activities obtained for the various fractions are shown in FIG. 2. Activity was found in a large number of fractions.

The active fractions were further examined by acid-urea PAGE (AU-PAGE) and SDS PAGE. Results of these analyses showed that active antimicrobial peptides of the appropriate molecular weight were present and concentrated in fractions 76-78.

Figure 3:
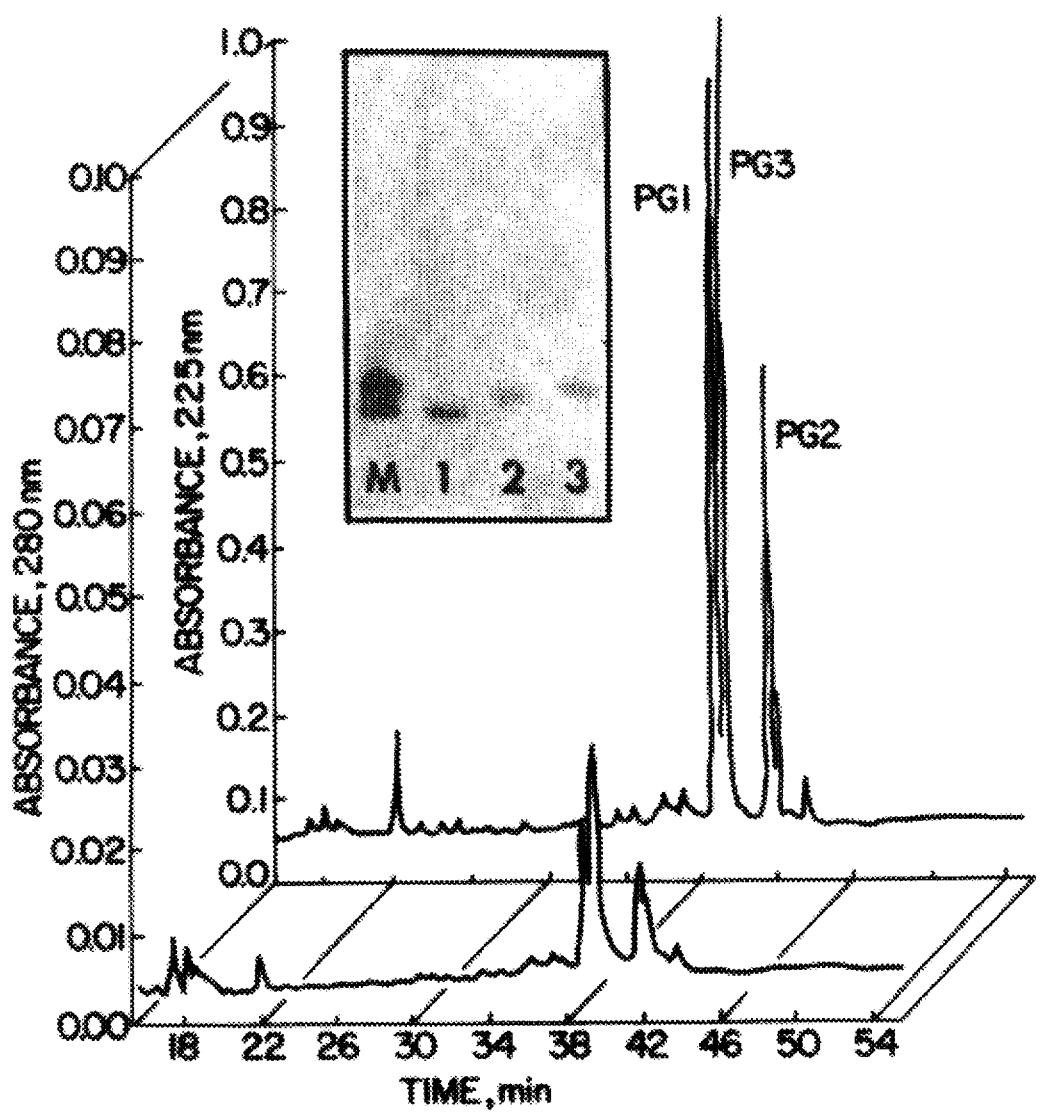
FIG. 3 shows an elution pattern obtained when fractions 76–78 from the Biogel P10 column of FIG. 1 is applied to HPLC.

Fractions 76-78 from the Biogel P10 column were then pooled and chromatographed on a 1×25 cm Vydac 218 TP1010 column with a gradient (buffer A is 0.1% TFA; buffer B is 0.1% TFA in acetonitrile) the increase in acetonitrile concentration was 1% per minute. The results, assessed in terms of absorbance at 280 nm and at 225 nm are shown in FIG. 3. The peaks corresponding the three peptides illustrated herein are labeled in the figure. The figure also contains an inset which shows the results of an acid-urea PAGE gel stained with Comassie Blue that contains a starting mixture composed of the pooled fractions and the individual PG species. These are labeled M, 1, 2 and 3 on the inset. The results clearly show the presence of three distinct proteins.

The isolated proteins were subjected to amino acid analysis using three independent methods, and to Edman degradation, chymotrypsin digestion, and fast atom bombardment mass spectrometric analysis. The peptides, named "protegrins", are shown to have the amino acid sequences as follows:

PG-1: RGGRLCYCRRRFCVCVGR (SEQ ID NO: 2)
PG-2: RGGRLCYCRRRFCICV (SEQ ID NO: 3)
PG-3: RGGGLCYCRRRFCVCVGR (SEQ ID NO: 4), and are amidated at the C-terminus.

The amidation status of the isolated peptides was established by synthesis of PG-3 both in the free carboxyl and carboxyamidated forms. These synthetic peptides were then compared to isolated PG-3 using AU-PAGE and also using reverse-phase HPLC. In both cases, the native product comigrated with the synthetic amidated form.

The antimicrobial proteins above are present in much lower concentrations in initial extracts than are the rabbit defensins in corresponding crude extracts where the defensins constitute more than 15% of the total protein in rabbit granulocytes. Using the AU-PAGE analytical method on the various stages of purification, the peptides are only faintly visible in the crude extracts, whereas corresponding crude extracts of rabbit granulocytes clearly show the presence of the defensins. The peptides of the invention become clearly evident only after the ultrafiltration step.

Because the protegrins whose structures are set forth above show sequence homology to the decapeptide region corresponding to residues 1-10 of rabbit defensin NP-3a in the decapeptide region at positions 4-13 of PG-3, the protegrins, and in particular PG-3, may share the property of defensin NP-3a in being capable of competitively antagonizing ACTH-mediated steroid synthesis by adrenocytes. This property called "corticostasis", may influence the effectiveness of the protegrins as antiinfectious agents when employed in vivo.

EXAMPLE 2

Antimicrobial Activity

Figure 4A:
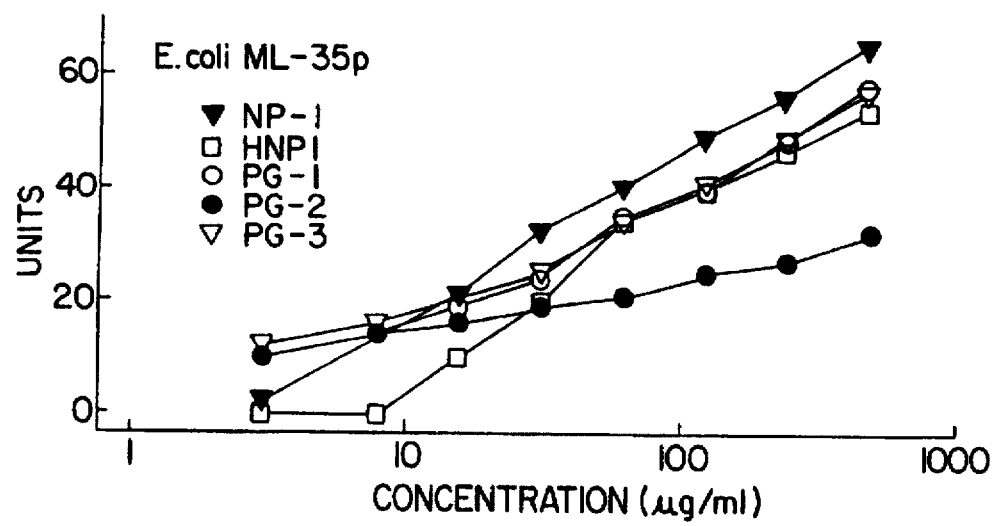
FIG. 4a shows antibacterial activity against E. Coli.
Figure 4B:
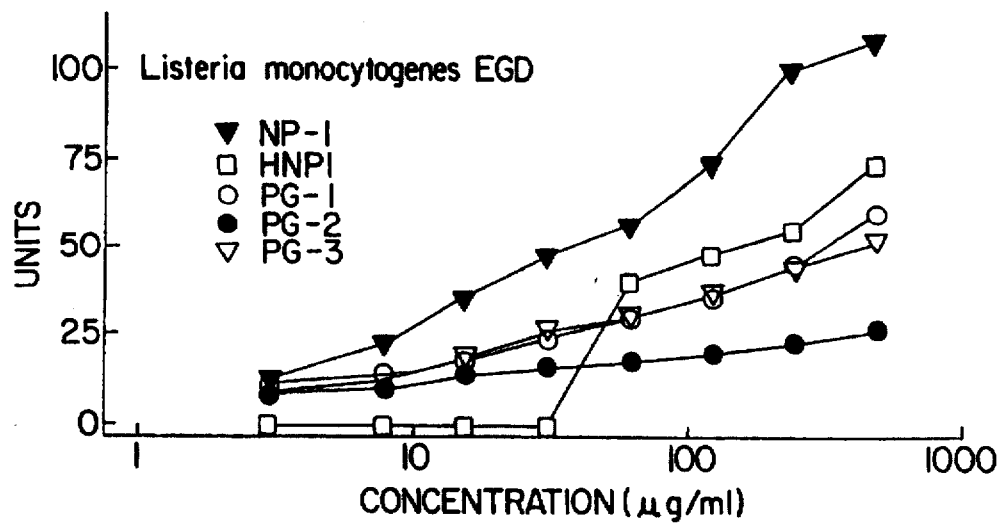
FIG. 4b shows antibacterial activity against Listeria monocytogenes.
Figure 4C:
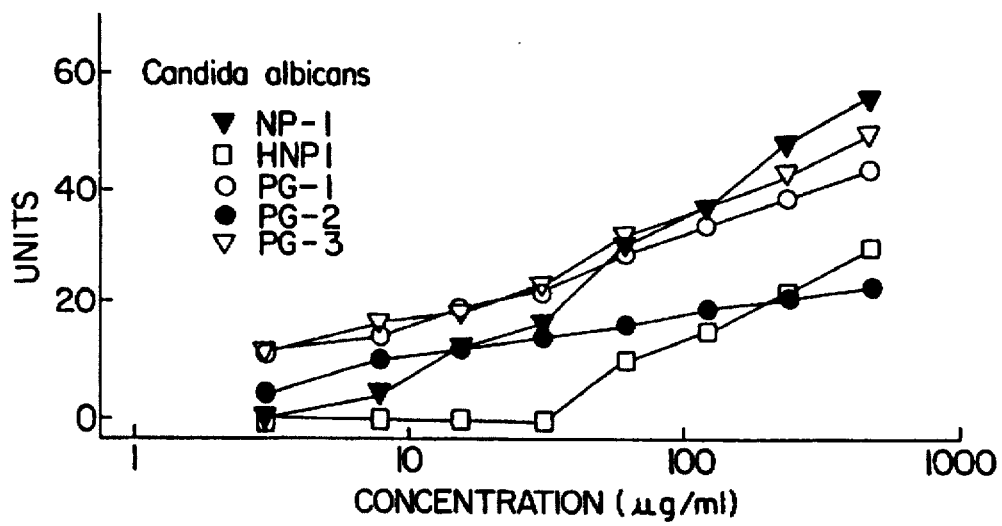
FIG. 4c shows antifungal activity against Candida albicans.

The radial diffusion assay in agarose gels described in Example 1 was also used to test the activity of the purified protegrins. FIGS. 4a, 4b and 4c show the results against three test organisms in units described as above. The rabbit defensin (NP-1) and the human defensin (HNP-1) were used as controls.

FIG. 4a shows that PG-1 and PG-3 are more effective against E. coli ML-35P than HNP-1 and only slightly less effective than NP-1. PG-1 and PH-3 were also effective against Listeria monocytogenes, strain EGD as shown in FIG. 4b. In FIG. 4c, PG-1 and PG-3 were also shown effective against Candida albicans. In general, these peptides are approximately as effective as rabbit defensin NP-1 on a weight basis and are more effective than HNP-1. In all cases, PG-2 was also effective against the three organisms tested but was not as active as the other two peptides.

EXAMPLE 3

Retention of Activity Under Certain Conditions

Figures 1, 5A:
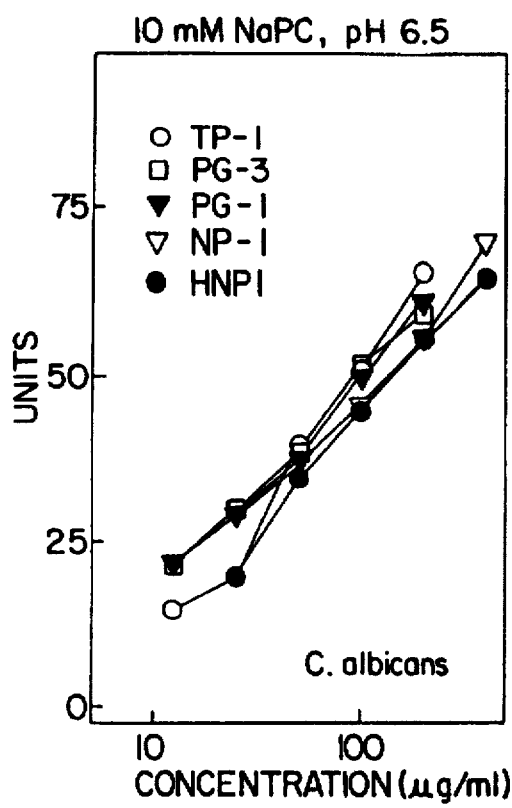
FIG. 5a shows activity against Candida albicans in 100 µM NaCl.
Figures 2, 5A:
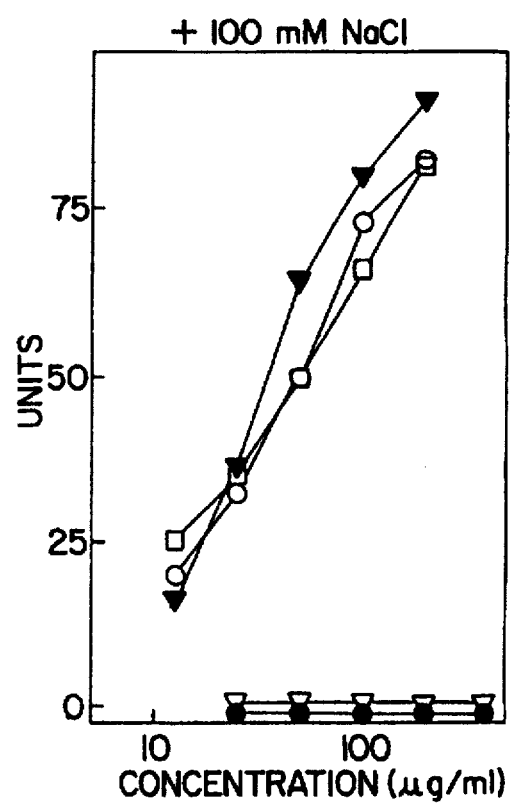
Figures 1, 5B:
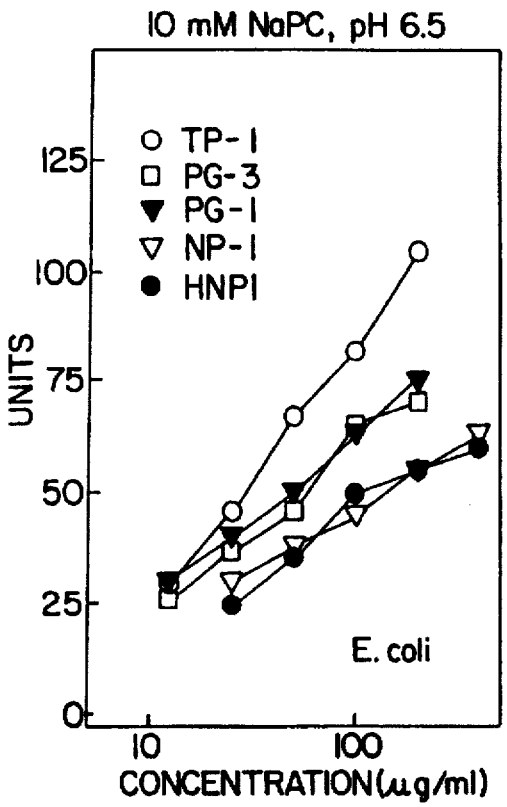
FIG. 5b shows activity against E. Coli in 100 µM NaCl.
Figures 2, 5B:
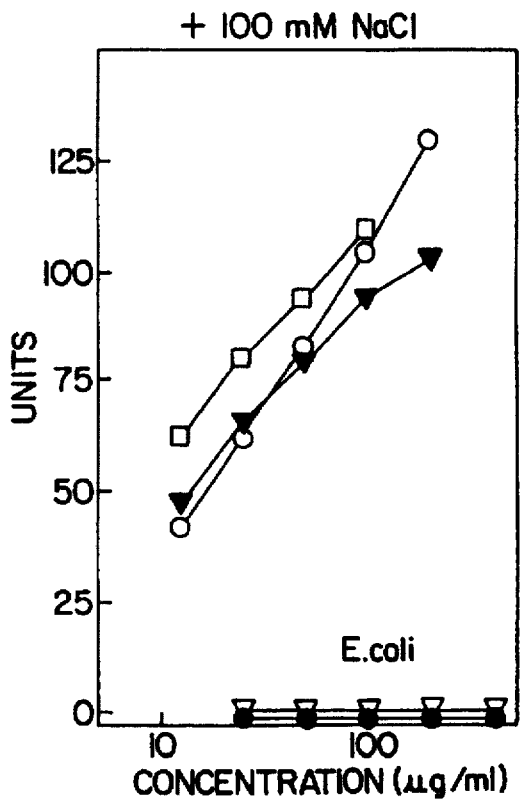
Figures 1, 5C:
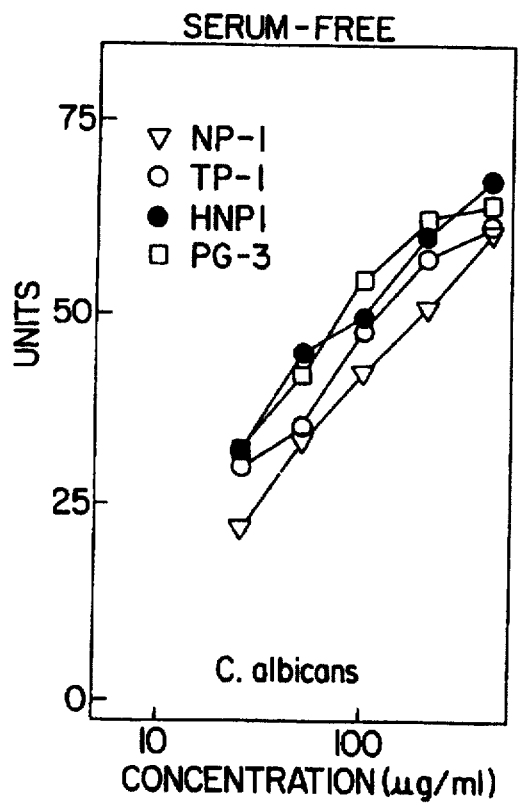
FIG. 5c shows activity against Candida albicans in 90% fetal calf serum.
Figures 2, 5C:
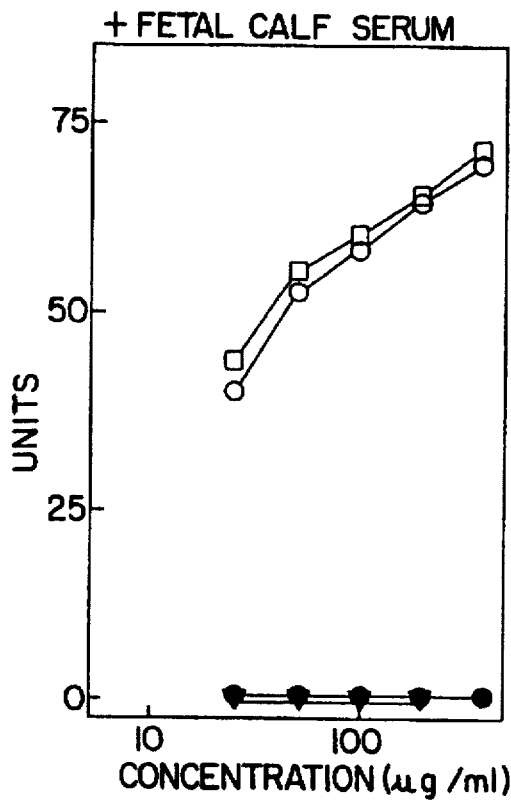

The antimicrobial activity of the invention compounds was tested as set forth above, but under conditions of 100 μM NaCl and in the presence of 90% fetal calf serum. FIGS. 5a and 5b show —that PG-1 and PG-3 retain their activity with respect to C. albicans and E. coli respectively, even in the presence of 100mM NaCl. Neither NP-1 nor HNP-1 have this property. FIG. 5c shows that although NP-1 and NHP-2 lose their ability to inactivate C. albicans in 90% fetal calf serum, inactivation by PG-3 is retained.

Accordingly, the protegrins of the invention retain their antimicrobial properties under useful physiological conditions, including isotonic and borate solutions appropriate for use in eye care products.

EXAMPLE 4

Ability to Bind Endotoxin

The protegrins of the invention were tested for their ability to bind the lipid polysaccharide (LPS) of the gram-negative bacterium E. coli strain 0.55B5. The assay was the Limulus amebocyte lysate (LAL) test for endotoxins conducted in the presence and absence of the test compounds. The test was conducted using the procedure described in Sigma Technical Bulletin No. 210 as revised in December 1992 and published by Sigma Chemical Company, St. Louis, Mo.

The LAL test is based on the ability of LPS to effect gelation in the commercial reagent E-Toxate™ which is prepared from the lysate of circulating amebocytes of the Horseshoe Crab Limulus polyphemus. As described in the technical bulletin, when exposed to minute quantities of LPS, the lysate increases in opacity as well as viscosity and may gel depending on the concentration of endotoxin. The technical bulletin goes on to speculate that the mechanism appears analogous to the clotting of mammalian blood and involves the steps of activation of a trypsin-like preclotting enzymes by the LPS in the presence of calcium ion, followed by enzymic modifications of a "coagulogen" by proteolysis to produce a clottable protein. These steps are believed tied to the biologically active or "pyrogenic" portion of the molecule. It has been shown previously that detoxified LPS (or endotoxin) gives a negative LAL test.

The test compounds were used at various concentrations from 0.25 μg-10 μg in a final volume of 0.2 ml and the test mixtures contained LPS at a final concentration of 0.05 endotoxin unit/ml and E-Toxate™ at the same concentration. The test compounds were incubated together with the LPS for 15 minutes before the E-Toxate™ was added to a final volume after E-Toxate™ addition of 0.2 ml. The tubes were then incubated for 30 minutes at 37° C. and examined for the formation of a gel.

Both isolated native protegrins (nPGs) and synthetically prepared protegrins (sPGs) were tested. The sPGs were prepared with a carboxyl group at the C-terminus or with an amidated C-terminus. The nPGs are amidated at the C-terminus. Also tested were six different rabbit defensins (NPs) and four native human defensins (HNPs). The results are shown in Table 1.

TABLE 1

| Peptide | 10 µg | 5 µg | 2.5 µg | 1.0 µg | 0.5 µg | 0.25 µg |
|---|---|---|---|---|---|---|
| nPG-1 | no gel | no gel | no gel | no gel | + | ++ |
| nPG-2 | no gel | no gel | no gel | no gel | + | ++ |
| nPG-3 | no gel | no gel | trace | ++ | ++ | ++ |
| sPG-3 acid | no gel | no gel | trace | ++ | ++ | ++ |
| sPG-3 amide | no gel | no gel | no gel | + | ++ | ++ |
| NP-1 | not tested | not tested | ++ | ++ | ++ | ++ |
| NP-2 | trace | + | + | ++ | ++ | ++ |
| NP-3a | no gel | no gel | no gel | ++ | ++ | ++ |
| NP-3b | no gel | no gel | + | ++ | ++ | ++ |
| NP-4 | not tested | not tested | + | ++ | ++ | . |
| NP-5 | no gel | trace | + | + | ++ | ++ |
| HNP-1 | no gel | + | + | ++ | ++ | ++ |
| HNP-2 | trace | trace | trace | + | + | ++ |
| HNP-3 | no gel | + | + | ++ | ++ | ++ |
| HNP-4 | no gel | trace | trace | ++ | + | ++ |

As seen from the results, all of the protegrins, both synthetic and native, and both in the amidated and nonamidated forms are able to bind sufficiently to LPS to prevent any substantial gel formation at concentrations as low as 2.5 µg/0.2 ml. nPG-1 and nPG-2 are effective at somewhat lower concentrations. The protegrins were substantially more effective than the NP or HNP test compounds; the most effective among these controls was NP-3a, a peptide whose primary sequence most closely resembles that of the protegrins.

In a follow-up experiment, the concentration of LPS was varied from 0.05–0.25 endotoxin units (E.U.) and synthetic PG-3 amide was used as the test compound. The results are shown in Table 2.

TABLE 2

| Endotoxin Units | 0.25 E.U. | 0.10 E.U. | 0.05 E.U. |
|---|---|---|---|
| sPG-3 amide (2.5 µg) | no gel | no gel | no gel |
| sPG-3 amide (1.0 µg) | no gel | no gel | no gel |
| sPG-3 amide (0.5 µg) | ++ | ++ | no gel |
| no added protein | ++ | ++ | ++ |

These results show that since inhibition of gelation can be overcome by increasing the concentration of LPS, interaction with LPS is responsible for the lack of gelation, rather than interfering with the gelation enzyme cascade.

EXAMPLE 5

Activity of Linearalized Forms nPG-1 and nPG-3 were converted to linear form using a reducing agent to convert the disulfide linkages to sulfhydryl groups, which were then stabilized by alkylating with iodoacetamide.

The ability of both cyclic and linearalized PG-1 and PG-3 to inhibit gelation in the standard LAL assay was assessed then as described in Example 4 and the results are shown in Table 3.

TABLE 3

| Peptide | 5 µg | 2.5 µg | 1.0 µg | 0.25 µg | |
|---|---|---|---|---|---|
| nPG-1 | no gel | no gel | ++ | ++ | ++ |
| cam-nPG-1 | no gel | no gel | ++ | ++ | ++ |
| nPG-3 | no gel | no gel | ++ | ++ | ++ |
| cam-nPG-3 | no gel | no gel | ++ | ++ | ++ |

These results show that the linearalized and cyclic forms of the protegrins are equally capable of inhibiting gelation and binding to endotoxin.

The antimicrobial activity of the linearalized forms was also compared with that of the native protegrins. Both linearalized and cyclic forms of the protegrins tested continue to show antimicrobial activity, although the effectiveness of these peptides as antimicrobials depends on the nature of the target organism and on the test conditions. The antimicrobial activity of native PG-1 and its linearalized form (cam-PG-1) and PG-3 and its linearalized form (cam-PG-3) were tested according to the procedure set forth in Example 1 as described by Lehrer, R. I. et al. *J Immunol Meth* (1991) 137:167–173. The results are set forth in FIGS. 6a–6f.

Figure 6A:
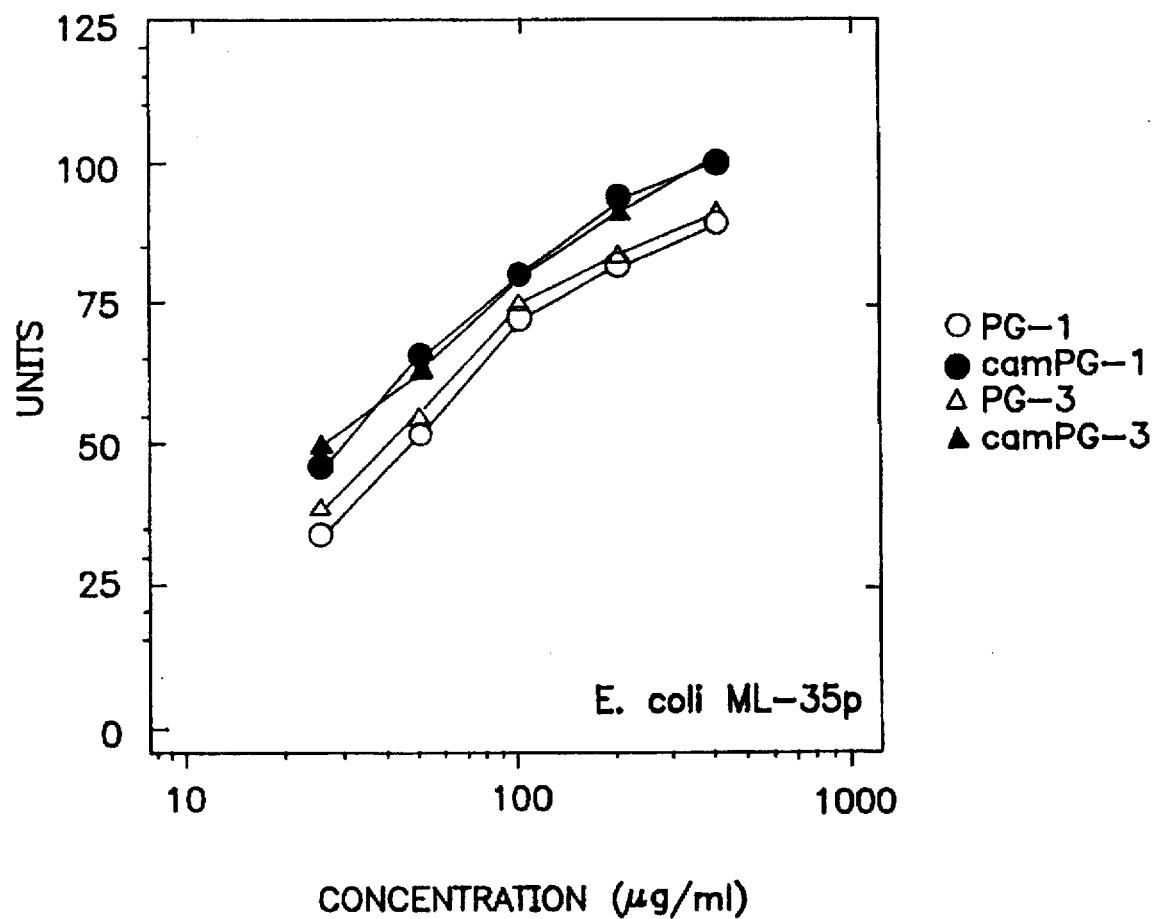
FIG. 6a shows the activity against E. coli in 10 mM phosphate-citrate buffer, pH 6.5.
Figure 6B:
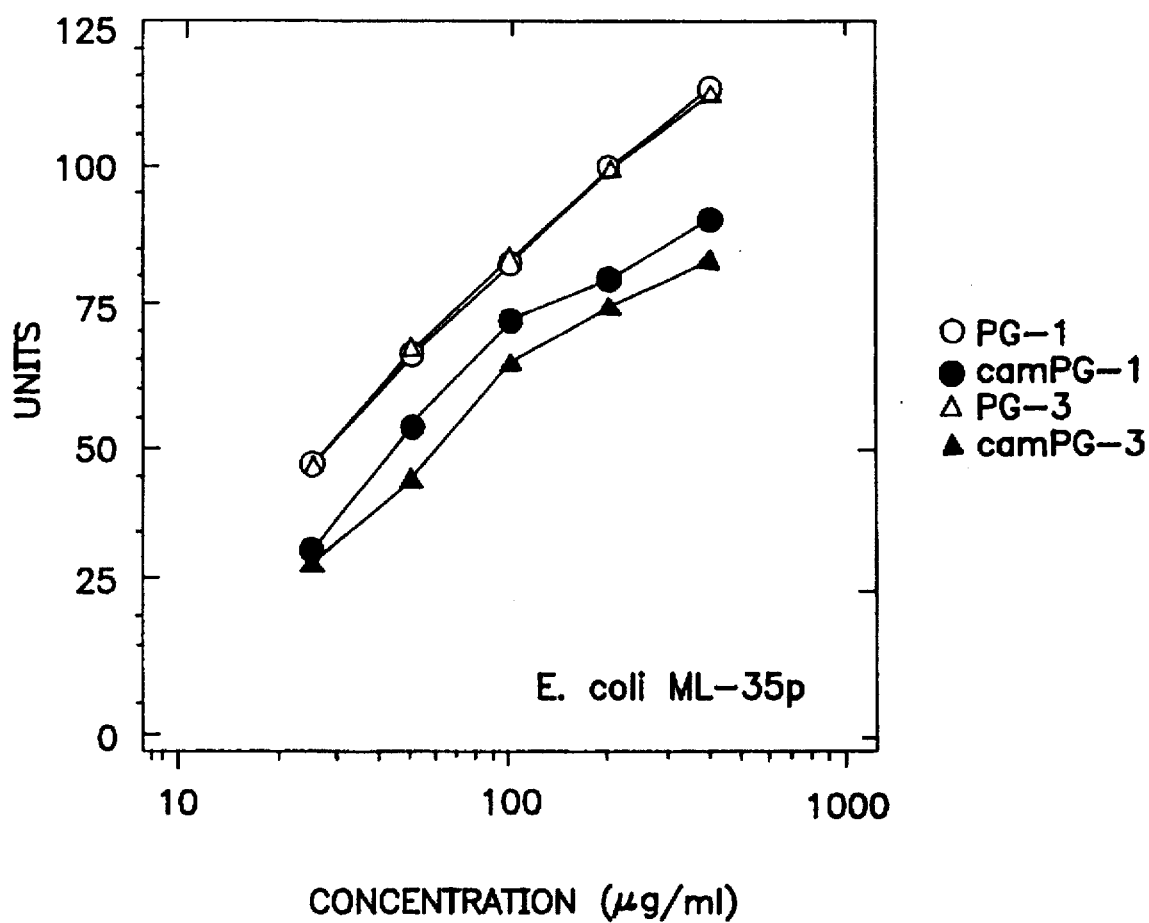
FIG. 6b shows the activity against E. coli in the same buffer with 100 mM NaCl.

FIGS. 6a and 6b show the antimicrobial activity of these peptides in the concentration range 20 µg/ml-125 µg/ml with respect to *E. coli* ML-35P either in 10 mM phosphate-citrate buffer, pH 6.5 (FIG. 6a) or in the presence of this buffer plus 100 mM NaCl (FIG. 6b). Both protegrins showed strong antimicrobial activity with respect to this organism; the linear form was slightly more potent in the presence of buffer alone than was the cyclic form; on the other hand, the cyclic form was more potent than the linear form under isotonic conditions.

Figure 6C:
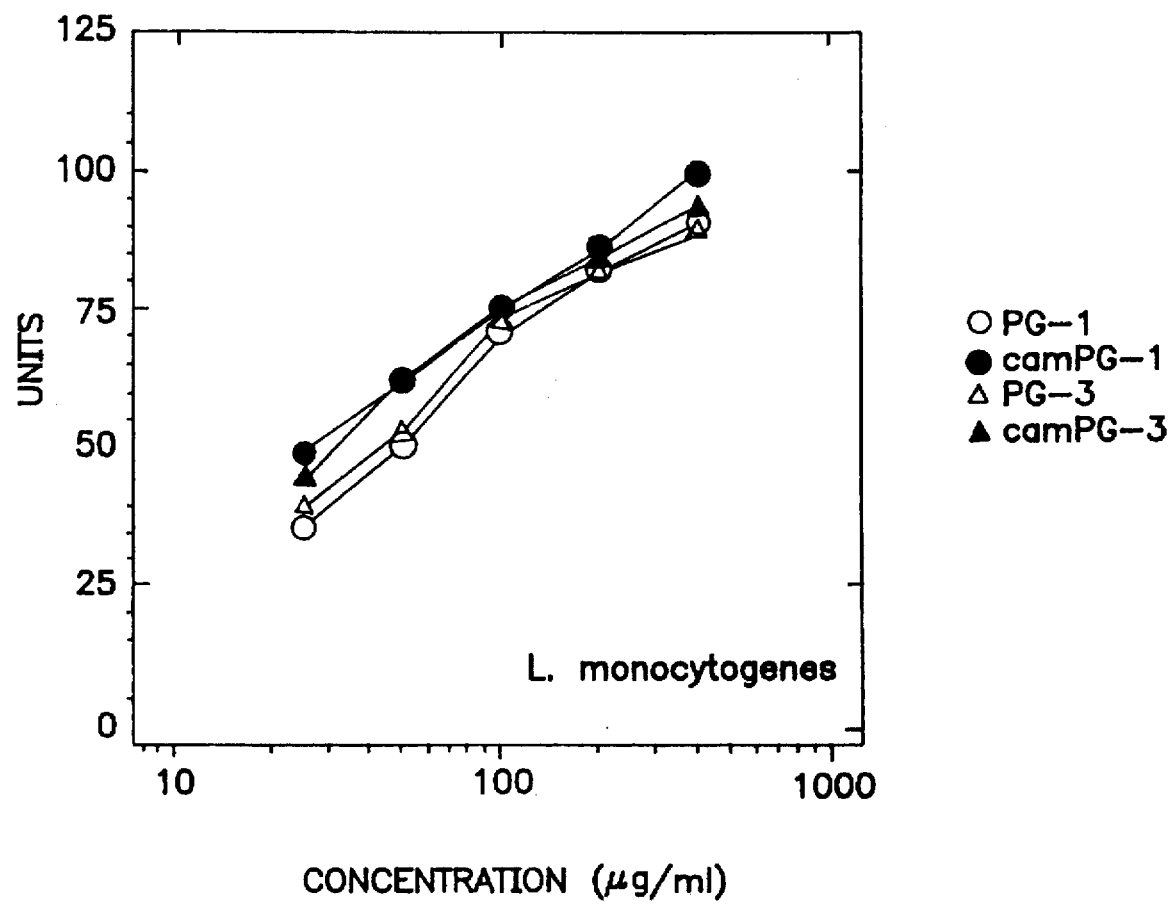
FIG. 6c shows the activity against L. monocytogenes in the buffer of FIGS. 6a–6b.
Figure 6D:
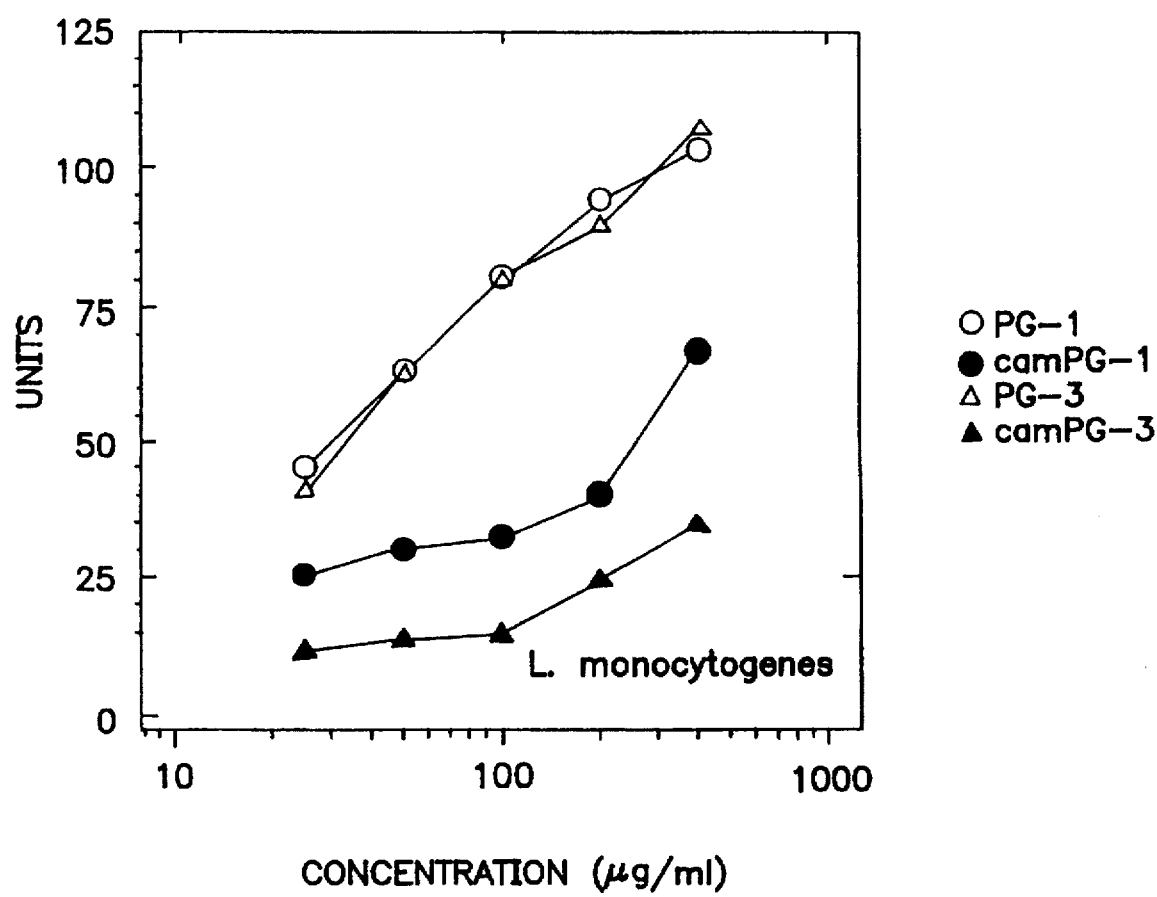
FIG. 6d shows the activity against L. monocytogenes in the same buffer with the addition of 100 mM NaCl.

FIGS. 6c and 6d show the antimicrobial effect with respect to *L. monocytogenes*. In FIG. 6c where the above-mentioned buffer alone was used, both cyclic and linearalized forms of the protegrins showed strong antimicrobial activity and both were approximately equally effective over the concentration range tested (20 µg/ml–125 µg/ml ).

FIG. 6d shows the effect with respect to *L. monocytogenes* in the presence of this buffer plus 100 mM NaCl over the same concentration range. The cyclic form retained strong antimicrobial activity with a slightly greater concentration dependence. Linearalization appeared to lower the activity appreciably although high concentrations were still able to show an antimicrobial effect.

Figure 6E:
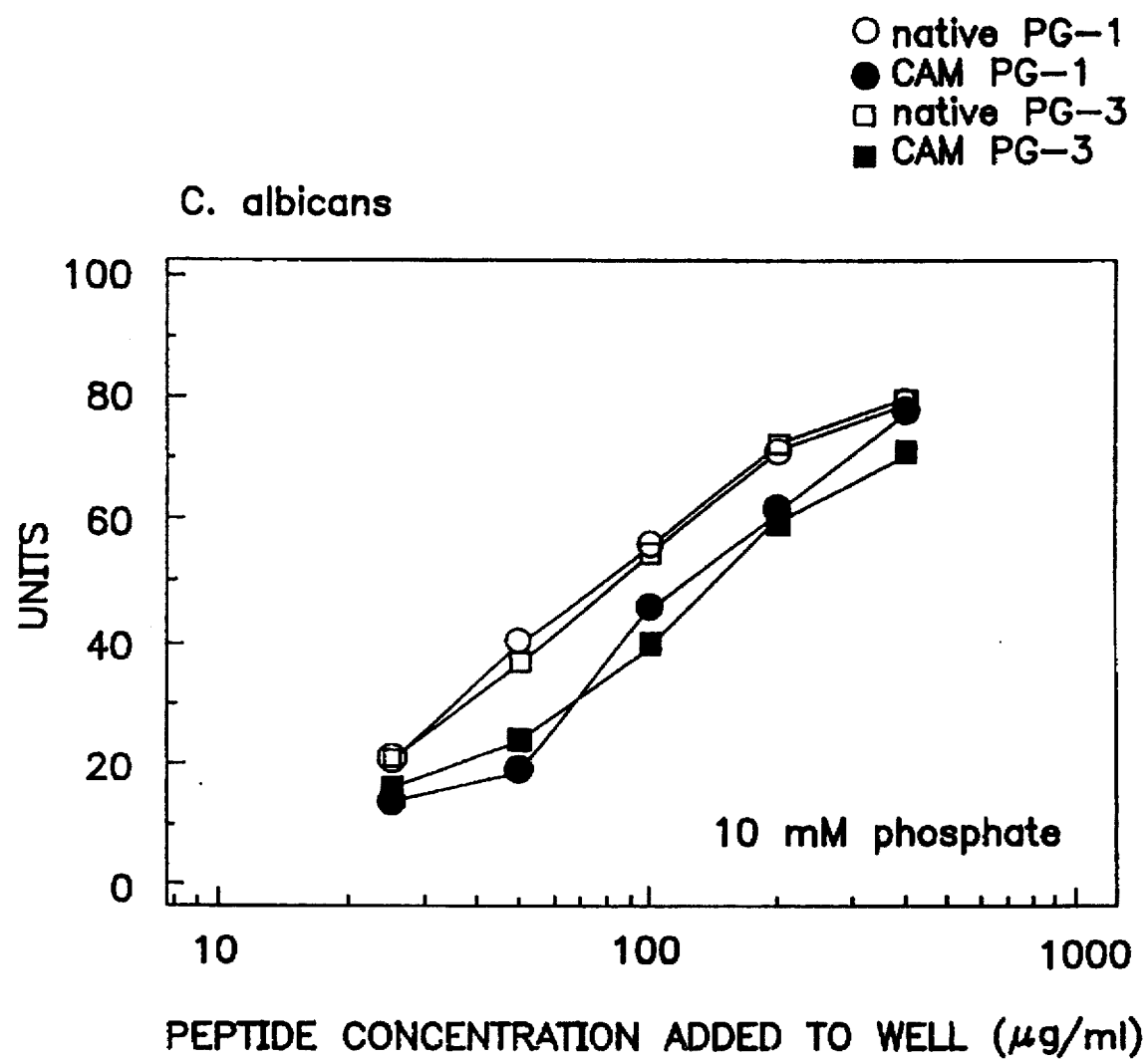
FIG. 6e shows the activity against C. albicans in the presence of 10 mM phosphate.
Figure 6F:
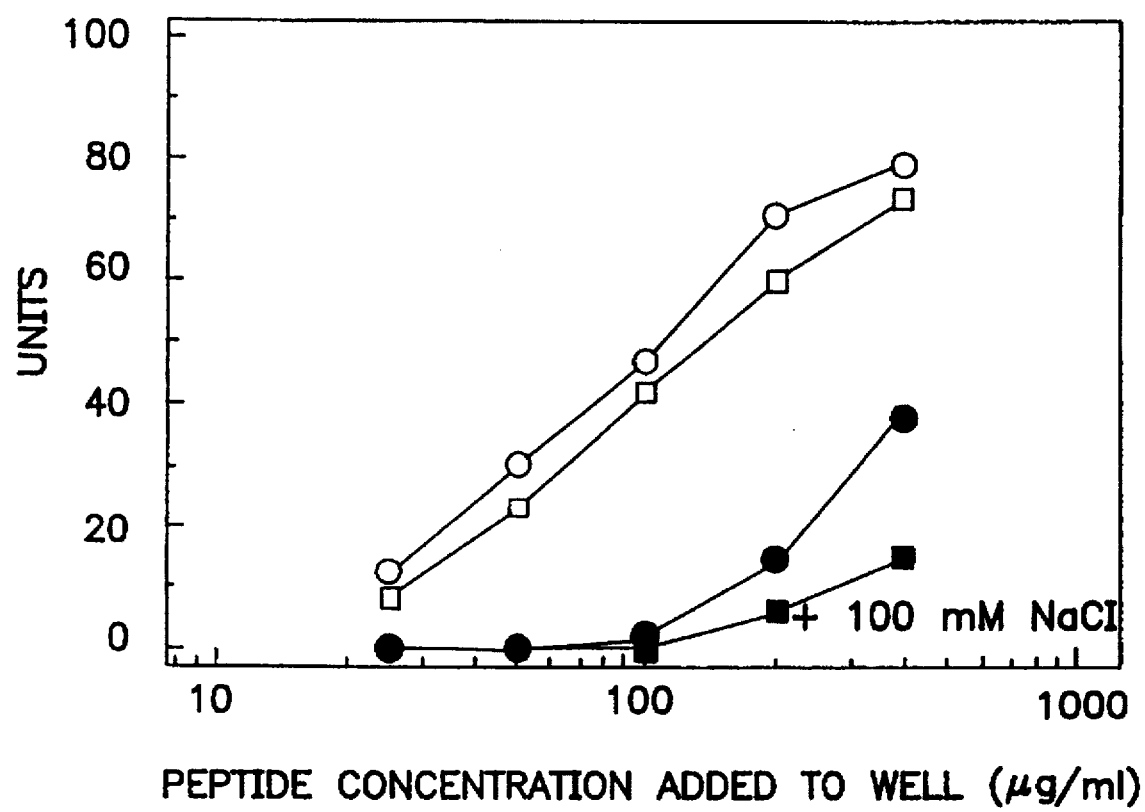
FIG. 6f shows the activity against C. albicans in the presence of 10 mM phosphate plus 100 mM NaCl.

The yeast *C. albicans* was tested with the results shown in FIGS. 6e and 6f. FIG. 6e shows that all forms of these protegrins were antimicrobial in a dose-dependent manner over the above concentration range when tested in the presence of 10 mM phosphate buffer alone, although the linearalized peptides were very slightly less effective. FIG. 6f shows the results of the same assay run in the presence of buffer plus 100 mM NaCl. While the cyclized forms retained approximately the same level of antimicrobial effect, the activity of the linearalized forms was greatly diminished so that at concentrations below 100 µg/ml of the protegrin, virtually no antimicrobial effect was seen. However, at higher concentrations of 130 µg/ml, a moderate antimicrobial effect was observed.

Thus, depending on the target microorganism and the conditions used, both the cyclized and linearalized forms of the protegrins have antimicrobial activity.

EXAMPLE 6

Antimicrobial Activity Under Conditions Suitable for Treatment of the Eye

Contact lens solutions are typically formulated with borate buffered physiological saline and may or may not contain EDTA in addition. Protegrins in the form of the synthetic PG-3 amide and synthetic PG acid were tested generally in the assay described in Example 1 wherein all underlay gels contain 25 mM borate buffer, pH 7.4, 1% (v/v) trypticase soy broth (0.3 mg/ml TSB powder) and 1% agarose. Additions included either 100 mM NaCl, 1 mM EDTA or a combination thereof. Other test compounds used as controls were the defensin NP-1 and lysozyme. Dose response curves were determined.

Table 4 shows the estimated minimal bacteriocidal concentrations in μg/ml of the various test compounds.

TABLE 4

| ESTIMATED MINIMAL FUNGICIDAL CONCENTRATIONS (μg/ml) | | | | |
|---|---|---|---|---|
| Peptide | buffer | + EDTA | + NaCl | + EDTA & NaCl |
| sPG-3 amide | 13.0 | 9.5 | 4.1 | 3.1 |
| sPG-3 acid | 15.0 | 9.5 | 4.6 | 3.7 |
| NP-1 | 35.0 | 45.0 | >200 | >200 |
| lysozyme | 75.0 | 45.0 | >200 | >200 |

Although protegrins are somewhat less active in 25 mM borate buffered saline than in 25 mM phosphate buffer, the antimicrobial activity is enhanced by adding physiological saline and modestly enhanced by 1 mM EDTA, as shown in the table.

A similar test was run with *Candida albicans* as the target organism with the results shown in Table 5, which also shows estimates of minimal fungicidal concentrations.

TABLE 5

| ESTIMATED MINIMAL FUNGICIDAL CONCENTRATIONS (μg/ml) | | | |
|---|---|---|---|
| Peptide | 25 mM borate buffer | borate buffer + 120 mM NaCl | borate buffer + EDTA & NaCl |
| nPG-3 | 32.0 | 9.0 | 8.0 |
| sPG-3 amide | 19.0 | 7.7 | 7.0 |
| sPG-3 acid | 19.0 | 9.2 | 9.3 |
| NP-1 | 23.0 | 60.0 | 65.0 |
| HNP-1 | 25.0 | >200 | >200 |

Table 6 shows results of similar experiments conducted with *L. monocytogenes* as the target.

TABLE 6

| ESTIMATED MINIMAL BACTERICIDAL CONCENTRATIONS (μg/ml) | | | |
|---|---|---|---|
| Peptide | 25 mM borate buffer | borate buffer + 120 mM NaCl | borate buffer + EDTA & NaCl |
| nPG-3 | 25.0 | 7.0 | 5.7 |
| sPG-3 amide | 21.0 | 5.7 | 5.2 |
| sPG-3 acid | 30.0 | 7.0 | 7.0 |
| NP-1 | 20.0 | 11.0 | 3.8 |
| HNP-1 | 11.0 | >200 | >200 |

The results shown indicate that these compounds are capable of exerting their antimicrobial effects under conditions typically associated with conditions suitable for eye care products.

---

We claim:

1. A purified and isolated DNA which encodes the amino acid sequence $$A_1-A_2-A_3-A_4-A_5-C-A_7-C-A_9-A_{10}-A_{11}-A_{12}-C-A_{14}-C-A_{16}-(A_{17}-A_{18}) \quad (1)(SEQ\ ID\ NO:1)$$

wherein $A_1$, $A_9$, $A_{10}$ and $A_{11}$ are basic amino acids;

$A_2$ and $A_3$ are small amino acids;

$A_5$, $A_7$, $A_{12}$, $A_{14}$ and $A_{16}$ are hydrophobic amino acids; and $A_4$ is a basic or a small amino acid;

$A_{17}$ is not present or, if present, is a small amino acid;

$A_{18}$ is not present or, if present, is a basic amino acid wherein a peptide comprising said amino acid sequence has antimicrobial activity against *E. coli*, *L. monocytogenes*, or *Candida albicans*.

2. A recombinant expression system for production of a peptide of the amino acid sequence $$A_1-A_2-A_3-A_4-A_5-C-A_7-C-A_9-A_{10}-A_{11}-A_{12}-C-A_{14}-C-A_{16}-(A_{17}-A_{18}) \quad (1)(SEQ\ ID\ NO:1)$$

wherein $A_1$, $A_9$, $A_{10}$ and $A_{11}$ are basic amino acids;

$A_2$ and $A_3$ are small amino acids;

$A_5$, $A_7$, $A_{12}$, $A_{14}$ and $A_{16}$ are hydrophobic amino acids; and $A_4$ is a basic or a small amino acid;

$A_{17}$ is not present or, if present, is a small amino acid;

$A_{18}$ is not present or, if present, is a basic amino acid wherein a peptide comprising said amino acid sequence has antimicrobial activity against *E. coli*, *L. monocytogenes*, or *Candida albicans*.

which expression system comprises a nucleotide sequence encoding said peptide operably linked to control sequences for effecting expression.

3. A recombinant host cell modified to contain the expression system of claim 2.

4. A method to produce an antimicrobial or antiviral or intermediate peptide which method comprises culturing the modified host cells of claim 3 under conditions wherein said peptide is produced; and recovering the peptide from the culture.

5. The method of claim 4 which further comprises effecting cystine linkages of said peptide and/or modifying the N-terminus and/or C-terminus of said peptide.

6. The method of claim 4 or 5 wherein in the amino acid sequence of formula (1), each of $A_1$, $A_9$, $A_{10}$ and $A_{11}$ is independently selected from the group consisting of R and K.

7. The method of claim 4 or 5 wherein each of $A_1$, $A_9$, $A_{10}$ and $A_{11}$ is R.

8. The method of claim 4 or 5 wherein in formula (1) each of $A_2$ and $A_3$ is independently selected from the group consisting of G, A, S and T.

9. The method of claim 4 or 5 wherein each of $A_2$ and $A_3$ is G.

10. The method of claim 4 or 5 wherein in formula (1), $A_4$ is R or G.

11. The method of claim 4 or 5 wherein in formula (1) each of $A_5$, $A_{14}$ and $A_{16}$ of formula (1) is independently selected from the group consisting of I, V and L.

12. The method of claim 4 or 5 wherein $A_5$ is L and $A_{16}$ is V and $A_{14}$ is I or V.

13. The method of claim 4 or 5 wherein in formula (1) each of $A_7$ and $A_{12}$ is independently selected from the group consisting of W, Y, and F.

14. The method of claim 4 or 5 wherein $A_7$ is Y or $A_{12}$ is F.

15. The method of claim 4 or 5 wherein, in formula (1)

each of $A_1$, $A_9$, $A_{10}$ and $A_{11}$ is independently selected from the group consisting of R and K;

each of $A_2$ and $A_3$ is independently selected from the group consisting of G, A, S and T; $A_4$ is R or G;

each of $A_5$, $A_{14}$ and $A_{16}$ is independently selected from the group consisting of I, V and L; and each of $A_7$ and $A_{12}$ is independently selected from the group consisting of W, Y and F.

16. The method of claim 15 wherein each of $A_1$, $A_9$, $A_{10}$ and $A_{11}$ is R;

each of $A_2$ and $A_3$ is G;

$A_4$ is R or G; and $A_7$ is Y or $A_{12}$ is F.

17. The method of claims 4 or 5 wherein the amino acid sequence of formula (1) is selected from the group consisting of

PG-1: RGGRLCYCRRRFCVCVGR (SEQ ID NO:2)

PG-2: RGGRLCYCRRRFCICV (SEQ ID NO:3)

PG-3: RGGGLCYCRRRFCVCVGR (SEQ ID NO:4).

* * * * *

UNITED STATES PATENT AND TRADEMARK OFFICE

CERTIFICATE OF CORRECTION

PATENT NO. : 5,693,486

DATED : 2 December 1997

INVENTOR(S) : Robert I. Lehrer, Vladimir N. Kokryakov and Sylvia S. L. Harwig

It is certified that error appears in the above-identified patent and that said Letters Patent is hereby corrected as shown below:

On the front page of the patent, line [73] Assignee, delete "IntraBiotics, Sunnyvale, Calif." and insert therefor --University of California, Los Angeles, California.--

Signed and Sealed this

Tenth Day of April, 2001

Attest:

NICHOLAS P. GODICI

Attesting Officer   Acting Director of the United States Patent and Trademark Office